(12) United States Patent
Yamazaki

(10) Patent No.: US 10,046,291 B2
(45) Date of Patent: Aug. 14, 2018

(54) METHOD FOR MANUFACTURING MICROCAPSULES

(71) Applicant: KAO CORPORATION, Tokyo (JP)

(72) Inventor: Daisuke Yamazaki, Wakayama (JP)

(73) Assignee: KAO CORPORATION, Tokyo (JP)

(*) Notice: Subject to any disclaimer, the term of this patent is extended or adjusted under 35 U.S.C. 154(b) by 0 days.

(21) Appl. No.: 15/100,909

(22) PCT Filed: Dec. 5, 2014

(86) PCT No.: PCT/JP2014/082323
§ 371 (c)(1),
(2) Date: Jun. 1, 2016

(87) PCT Pub. No.: WO2015/083836
PCT Pub. Date: Jun. 11, 2015

(65) Prior Publication Data
US 2016/0303531 A1      Oct. 20, 2016

(30) Foreign Application Priority Data

Dec. 6, 2013    (JP) ................................. 2013-252838

(51) Int. Cl.
| | |
|---|---|
| *A61L 9/04* | (2006.01) |
| *A61K 8/00* | (2006.01) |
| *B01J 13/22* | (2006.01) |
| *A61K 8/11* | (2006.01) |
| *A61K 8/25* | (2006.01) |
| *A61K 8/58* | (2006.01) |
| *A61Q 13/00* | (2006.01) |
| *A61Q 19/00* | (2006.01) |
| *B01J 13/06* | (2006.01) |
| *B01J 13/18* | (2006.01) |
| *C09B 67/02* | (2006.01) |
| *C09D 183/02* | (2006.01) |
| *C11B 9/00* | (2006.01) |
| *C11D 3/50* | (2006.01) |
| *C11D 17/00* | (2006.01) |
| *A23L 27/00* | (2016.01) |

(52) U.S. Cl.
CPC .............. *B01J 13/22* (2013.01); *A23L 27/72* (2016.08); *A61K 8/11* (2013.01); *A61K 8/25* (2013.01); *A61K 8/585* (2013.01); *A61Q 13/00* (2013.01); *A61Q 19/00* (2013.01); *B01J 13/06* (2013.01); *B01J 13/18* (2013.01); *C09B 67/0097* (2013.01); *C09D 183/02* (2013.01); *C11B 9/00* (2013.01); *C11D 3/50* (2013.01); *C11D 3/505* (2013.01); *C11D 17/0039* (2013.01); *A61K 2800/412* (2013.01)

(58) Field of Classification Search
CPC ..... B01J 3/22; B01J 13/06; B01J 13/22; B01J 13/18; A61K 8/585; A61K 8/11; A61K 8/125; A61K 2800/412; C11D 3/505; C11D 17/0039; C11D 3/50; C09D 183/02; A61Q 13/00; A61Q 19/00; A23L 27/72; C09B 67/0097
USPC ........................................................ 512/4, 1
See application file for complete search history.

(56) References Cited

U.S. PATENT DOCUMENTS

| | | | |
|---|---|---|---|
| 6,337,089 B1 | 1/2002 | Yoshioka et al. | |
| 2008/0317795 A1 | 12/2008 | Traynor et al. | |
| 2010/0143422 A1 | 6/2010 | Popplewell et al. | |
| 2010/0204342 A1 | 8/2010 | Kawasaki et al. | |
| 2010/0247660 A1* | 9/2010 | Lei .......................... | B01J 13/18 424/490 |
| 2011/0158923 A1 | 6/2011 | Galeone et al. | |
| 2011/0293677 A1 | 12/2011 | Bekemeier et al. | |

(Continued)

FOREIGN PATENT DOCUMENTS

| | | |
|---|---|---|
| JP | 2000-225332 A | 8/2000 |
| JP | 2003-534249 A | 11/2003 |

(Continued)

OTHER PUBLICATIONS

Takao et al, WO 2010055632 Machine Translation, May 20, 2010.*

(Continued)

*Primary Examiner* — Jessica Whiteley
(74) *Attorney, Agent, or Firm* — Oblon, McClelland, Maier & Neustadt, L.L.P.

(57) ABSTRACT

The present invention provides a process for producing microcapsules capable of retaining an organic compound as an active ingredient such as fragrance materials therein over a long period of time. The present invention relates to process for producing microcapsules, which includes step (1) of emulsifying an organic phase including at least one organic compound and a tetraalkoxysilane such that a content of the tetraalkoxysilane in the organic phase is not less than 10% by mass and not more than 60% by mass on the basis of the organic compound, in a water phase inducing a surfactant, and subjecting the resulting emulsion to a sol-gel reaction under acidic conditions to form capsules each including the core and the first shell; and step (2) of further adding a tetraalkoxysilane to a water dispersion containing the capsules obtained in the step (1), and subjecting the obtained mixture to a sol-gel reaction while maintaining an initial pH value in the sol-gel reaction of the step (2) below an initial pH value in the sol-gel reaction of the step (1) to form the capsules each including the second shell encapsulating the first shell.

19 Claims, 2 Drawing Sheets

(56) References Cited

U.S. PATENT DOCUMENTS

| | | | |
|---|---|---|---|
| 2012/0104638 A1* | 5/2012 | Traynor | B01J 13/18 264/4.32 |
| 2012/0104639 A1 | 5/2012 | Traynor et al. | |
| 2013/0095185 A1 | 4/2013 | Toledano et al. | |
| 2013/0181363 A1 | 7/2013 | Viaud-Massuard et al. | |
| 2013/0302413 A1* | 11/2013 | Marteaux | A45C 11/00 424/451 |
| 2014/0044760 A1 | 2/2014 | Lei et al. | |

FOREIGN PATENT DOCUMENTS

| | | | |
|---|---|---|---|
| JP | 2005-526025 A | | 9/2005 |
| JP | 2007-500590 A | | 1/2007 |
| JP | 2010-528990 A | | 8/2010 |
| JP | 2012-501849 A | | 1/2012 |
| JP | 2012-505752 A | | 3/2012 |
| JP | 2013-215685 A | | 10/2013 |
| JP | 2013-538683 A | | 10/2013 |
| WO | 2010/055632 A1 | | 5/2010 |
| WO | 2010055632 | * | 5/2010 |
| WO | WO 2011/091285 A1 | | 7/2011 |
| WO | 2011124706 | * | 10/2011 |

OTHER PUBLICATIONS

International Search Report dated Mar. 17, 2015 in PCT/JP14/082323 filed Dec. 5, 2014.

Partial supplementary European search report dated Apr. 21, 2017 in patent application No. 14868446.7.

Ikuo Moriguchi, et al., "Simple Method of Calculating Octanol/Water Partition Coefficient", Chem. Pharm. Bull. 40(1), (1992), pp. 127-130.

OECD Guideline TG117, OECD/ODCE, OECD Guidelines for the Testing of Chemicals, Adopted: Apr. 13, 2004, 11 pp.

Butane (liquefied)(cylinder), ICSC:0232 Peer-Review Status: Nov. 27, 2003 Validated, IPCS, 2 pp.

1-Butanol, ICSC:0111 Peer-Review Status: Apr. 19, 2005 Validated, IPCS, 3 pp.

1-Propanol, ICSC:0553 Peer-Review Status: Oct. 20, 1999 Validated, IPCS, 2 pp.

N-Pentane, ICSC: 0534 Peer-Review Status:Apr. 11, 2014 Validated, IPCS, 3 pp.

Propane (liquefied)(cylinder), ICSC:0319 Peer-Review Status:Nov. 27, 2003 Validated, IPCS, 2 pp.

Supplementary European Search Report dated Jun. 21, 2017 issued in the corresponding European patent application No. 14868446.7.

* cited by examiner

METHOD FOR MANUFACTURING MICROCAPSULES

CROSS REFERENCE TO RELATED APPLICATION

This application is a 371 of PCT/JP2014/082323, filed on Dec. 5, 2014, and claims priority to Japanese Patent Application No. 2013-252838, filed on Dec. 6, 2013.

FIELD OF THE INVENTION

The present invention relates to a process for producing microcapsules, and microcapsules produced by the process.

BACKGROUND OF THE INVENTION

Hitherto, it has been attempted that fragrance materials (perfumes) or medical ingredients, etc., are encapsulated in microcapsules, prolonged their effects by being incorporated in products. In particular, one of important properties of fabric treatment products, cosmetics and detergents is to impart fragrance to clothes or human body, and therefore there is an increasing demand for products having a high persistence of fragrance.

Under these circumstances, there have been conventionally made intense studies on synthesis of the microcapsules by a sol-gel method.

For example, JP 2007-500590A aims at enjoying a benefit of a light-absorbing capability of sunscreens while substantially isolating the sunscreens, in particular, sunscreen active ingredients, from living tissues, and discloses microcapsules having a core material encapsulated within a microcapsule shell, the core material including an active ingredient, wherein the microcapsule shell includes an inorganic polymer constituted of polymerized precursors which is obtained by in-situ polymerization of the precursors, and the concentration of the core material based on a total weight of the microcapsules is not less than 95% w/w.

JP 2003-534249A discloses a therapeutic or cosmetic composition capable of stabilizing an active ingredient and delivering the ingredient which includes a plurality of microcapsules having a core-shell structure, wherein the microcapsules have a diameter of approximately 0.1 to 100 $\mu M$, wherein each core includes the active ingredient and is encapsulated within a microcapsule shell, and wherein the shell is constituted of an inorganic polymer obtained by a sol-gel process, and the microcapsule shell protects the active ingredient prior to topical application and releases the active ingredient from the microcapsules after topical application.

US 2010/0143422A aims, for example, at improving delivery of fragrance materials for various personal care products, and discloses a process for preparing microcapsule particles containing an active material in a core, the process including the steps of mixing a sol-gel precursor and an active material (in particular, essential oil); cooling the obtained mixture; then cooling a surfactant aqueous solution; adding the mixture of the sol-gel precursor and essential oil to the surfactant aqueous solution; emulsifying the resulting mixture; adding a defoamer to the emulsified mixture; and curing the mixture to form the microcapsule particles.

SUMMARY OF THE INVENTION

The present invention relates to the following aspects [1] and [2].

[1] A process for producing microcapsules each containing a first shell and a second shell which include silica as a constitutional component thereof, and a core including at least one organic compound which is encapsulated within the first shell, said process including the following steps (1) and (2);

step (1); emulsifying an organic phase including the at least one organic compound and a tetraalkoxysilane such that a content of the tetraalkoxysilane in the organic phase is not less than 10% by mass and not more than 60% by mass on the basis of the organic compound, in a water phase including a surfactant, and subjecting the resulting emulsion to sol-gel reaction under acidic conditions to form capsules each including the core and the first shell; and step (2): further adding a tetraalkoxysilane to a water dispersion containing the capsules obtained in the step (1), and subjecting the obtained mixture to sol-gel reaction while maintaining an initial pH value in the sol-gel reaction of the step (2) below an initial pH value in the sol-gel reaction of the step (1) to form the capsules each including the second shell encapsulating the first shell.

[2] Microcapsules each containing a core including at least one organic compound, a first shell encapsulating the core, and a second shell encapsulating the first shell, in which the first shell encapsulating the core includes silica as a constitutional component thereof and has a thickness of 5 to 20 nm; the second shell encapsulating the first shell includes silica as a constitutional component thereof and has a thickness of 10 to 100 nm; and the microcapsules have an average particle size of 0.5 to 50 $\mu m$.

DETAILED DESCRIPTION OF THE INVENTION

Microcapsules are in the form of very fine particles by themselves, and therefore have a very thin microcapsule shell (hereinafter also referred to merely as a "shell"). For this reason, there tends to occur such a problem that components of a core in the respective microcapsules are eluted therefrom into the outside environment owing to dissolution of the components into the shell or diffusion and penetration of the components through micropores present in the shell. In the sol-gel method, the microcapsules are obtained by forming a silica on a surface of respective emulsified oil droplets, and it is therefore possible to produce good microcapsules. However, the microcapsules obtained by the methods described in Patent Literatures 1 to 3 tend to fail to sufficiently retain an organic compound as an active ingredient such as fragrance materials to be encapsulated therein over a long period of time, probably owing to insufficient denseness or strength of a shell thereof.

The present invention relates to a process for producing microcapsules capable of retaining an organic compound as an active ingredient such as fragrance materials therein over a long period of time, and microcapsules obtained by the process.

The present inventors have found that by forming a shell of the respective microcapsules in two-stage process, it is possible to enhance denseness and strength of the shell as compared to those obtained in the conventional technologies, produce microcapsules each including a first shell that is formed of silica having a specific thickness, and a second shell having a mesoporous structure, and that the microcapsules are capable of retaining an organic compound constituting a core of the respective microcapsules over a long period of time.

That is, the present invention relates to the following aspects [1] and [2].

[1] A process for producing microcapsules each containing a first shell and a second shell which include silica as a constitutional component thereof, and a core including at least one organic compound which is encapsulated within the first shell, said process including the following steps (1) and (2):

step (1): emulsifying an organic phase including the at least one organic compound and a tetraalkoxysilane such that a content of the tetraalkoxysilane in the organic phase is not less than 10% by mass and not more than 60% by mass on the basis of the organic compound, in a water phase including a surfactant, and subjecting the resulting emulsion to sol-gel reaction under acidic conditions to form capsules each including the core and the first shell; and step (2): further adding a tetraalkoxysilane to a water dispersion containing the capsules obtained in the step (1), and subjecting the obtained mixture to sol-gel reaction while maintaining an initial pH value in the sol-gel reaction of the step (2) below an initial pH value in the sol-gel reaction of the step (1) to form the capsules each including the second shell encapsulating the first shell.

[2] Microcapsules each containing a core including at least one organic compound, a first shell encapsulating the core, and a second shell encapsulating the first shell, in which the first shell encapsulating the core includes silica as a constitutional component thereof and has a thickness of 5 to 20 nm; the second shell encapsulating the first shell includes silica as a constitutional component thereof and has a thickness of 10 to 100 nm; and the microcapsules have an average particle size of 0.5 to 50 μm.

In accordance with the present invention, there are provided a process for producing microcapsules capable of retaining an organic compound as an active ingredient such as fragrance materials to be encapsulated therein over a long period of time, and microcapsules obtained by the process.

PROCESS FOR PRODUCING MICROCAPSULES

Figure 1:
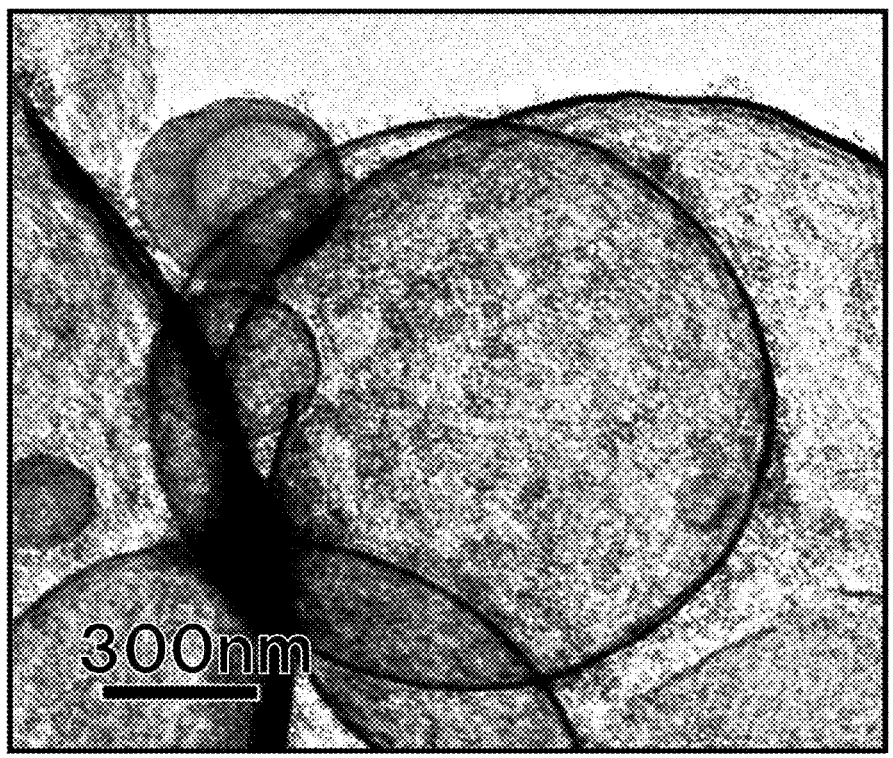
FIG. 1 is a micrograph of transmission electron microscope (TEM) showing microcapsules obtained in Example 1.

The process for producing microcapsules according to the present invention is such a process for producing microcapsules each containing a first shell and a second shell which include silica as a constitutional component thereof, and a core including at least one organic compound which is encapsulated within the first shell, and includes the following steps (1) and (2):

step (1): emulsifying an organic phase including the at least one organic compound and a tetraalkoxysilane such that a content of the tetraalkoxysilane in the organic phase is not less than 10% by mass and not more than 60% by mass on the basis of the organic compound, in a water phase including a surfactant, and subjecting the resulting emulsion to sol-gel reaction under acidic conditions to form capsules each including the core and the first shell; and step (2): further adding a tetraalkoxysilane to a water dispersion containing the capsules obtained in the step (1), and subjecting the obtained mixture to sol-gel reaction while maintaining an initial pH value in the sol-gel reaction of the step (2) below an initial pH value in the sol-gel reaction of the step (1) to form the capsules each including the second shell encapsulating the first shell.

The "sol-gel reaction" conducted in each of the steps (1) and (2) means the reaction in which the tetraalkoxysilane (i.e., a silica precursor) is subjected to hydrolysis and polycondensation reactions under acidic conditions, and thereby polymerized while eliminating an alcohol therefrom to synthesize silica constituting the first shell and the second shell.

<Step (1)>

The tetraalkoxysilane used in the step (1) is preferably a tetraalkoxysilane containing an alkoxy group having 1 to 3 carbon atoms, and more preferably tetraethoxysilane (hereinafter also referred to as "TEOS"), from the viewpoint of promoting the sol-gel reaction.

The amount of the tetraalkoxysilane used in the step (1) is not less than 10% by mass, preferably not less than 12% by mass, and more preferably not less than 14% by mass on the basis of the organic compound, and is also not more than 60% by mass, preferably not more than 50% by mass, more preferably not more than 40% by mass, and even more preferably not more than 35% by mass on the basis of the organic compound, from the viewpoint of promoting the sol-gel reaction.

It is considered that when the amount of the alkoxysilane added in the step (1) is not less than 10% by mass and not more than 60% by mass, it is possible to form a sufficiently dense layer of the first shell, and further prevent an excessive amount of the tetraalkoxysilane from remaining in the organic compound.

The core of the microcapsules according to the present invention includes at least one organic compound, preferably at least one material selected from the group consisting of a fragrance material, a fragrance precursor, an oil, an antioxidant, a cooling agent, a dye, a pigment, a silicone, a solvent and an oil-soluble polymer, more preferably at least one material selected from the group consisting of a fragrance material, a fragrance precursor, an oil, an antioxidant and a solvent, even more preferably at least one material selected from the group consisting of a fragrance material and a fragrance precursor, and further even more preferably a fragrance precursor.

The ClogP value of the aforementioned organic compound is preferably not less than 2, more preferably not less than 3, and even more preferably not less than 4, and is also preferably not more than 30, more preferably not more than 20, and even more preferably not more than 10. When the ClogP value of the organic compound is not less than 2, it is possible to enhance a rate of encapsulating the organic compound within the microcapsules (hereinafter also referred to merely as an "encapsulation rate") in the below-mentioned sol-gel reaction in the oil-in-water type emulsion. Similarly, in the case where the organic compound is in the form of a fragrance composition containing a plurality of fragrance materials, by controlling the ClogP value of the fragrance composition to not less than 2, it is also possible to enhance the rate of encapsulating the fragrance composition within the microcapsules (encapsulation rate) obtained by the sol-gel reaction.

The "ClogP value" as used herein means a "calculated log P (ClogP)" obtained by the method described in A. Leo, "Comprehensive Medicinal Chemistry", Vol. 4, C. Hansch, P. G. Sammems, J. B. Taylor and C. A. Ramsden, Eds., p. 295, Pergamon Press, 1990, and more specifically, the ClogP value is calculated according to Program CLOGP v. 4.01. In the case of using the fragrance composition containing a plurality of fragrance materials as the organic compound, the cLogP value of the fragrance composition is determined from a sum of values obtained by multiplying clogP values of the respective fragrance materials by volume ratios thereof in the fragrance composition.

Examples of the fragrance precursor include compounds capable of releasing fragrance components by reacting with water, etc. Specific examples of the fragrance precursor include silicic acid ester compounds containing an alkoxy component derived from a fragrance alcohol, fatty acid ester compounds containing an alkoxy component derived from a fragrance alcohol, acetal compounds or hemiacetal compounds obtained by the reaction between a carbonyl component derived from a fragrance aldehyde or a fragrance ketone and an alcohol compound, shiff base compounds obtained by the reaction between a carbonyl component derived from a fragrance aldehyde or a fragrance ketone and a primary amine compound, and hemiaminal compounds or hydrazone compounds obtained by the reaction between a carbonyl component derived from a fragrance aldehyde or a fragrance ketone and a hydrazine compound.

In addition, the other configuration of the fragrance precursor includes compounds capable of releasing fragrance components by reacting with light. Examples of the fragrance precursor of the above type include 2-nitrobenzyl ether compounds containing an alkoxy component derived from a fragrance alcohol, α-ketoester compounds containing a carbonyl component derived from a fragrance aldehyde or a fragrance ketone, and coumalic acid ester compounds containing an alkoxy component derived from a fragrance alcohol. These fragrance precursors may be used, for example, in the form of a polymer such as a reaction product obtained by the reaction between a part of carboxy groups of a polyacrylic acid and a fragrance alcohol. Of these fragrance precursors, the silicic acid ester compounds containing an alkoxy component derived from a fragrance alcohol are preferably used.

The surfactant used in the step (1) is preferably a cationic surfactant.

As the cationic surfactant, there may be mentioned compounds containing a nitrogen-based cationic group, and surfactants that tend to be rendered cationic by controlling a pH thereof. Specific examples of the cationic surfactant include alkylamine salts and quaternary ammonium salts. The number of carbon atoms in the alkyl group is preferably from 10 to 22, more preferably from 12 to 20, and even more preferably from 14 to 18.

Examples of the alkylamine salts include laurylamine acetate and stearylamine acetate. Examples of the quaternary ammonium salts include alkyltrimethylammonium chlorides such as lauryltrimethylammonium chloride, stearyltrimethylammonium chloride and cetyltrimethylammonium chloride, dialkyldimethylammonium chlorides such as distearyldimethylammonium chloride, and alkylbenzyldimethylammonium chlorides.

Of these cationic surfactants, particularly preferred are the quaternary ammonium salts.

The initial pH value in the sol-gel reaction of the step (1) is preferably not less than 3.5, and more preferably not less than 3.7, and is also preferably not more than 4.3, and more preferably not more than 3.9.

In the "sol-gel reaction" which is conducted using TEOS as the tetraalkoxysilane, the hydrolysis reaction and polycondensation reaction are allowed to proceed under acidic conditions as follows.

Hydrolysis Reaction:

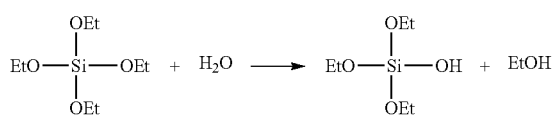

Condensation Reaction:

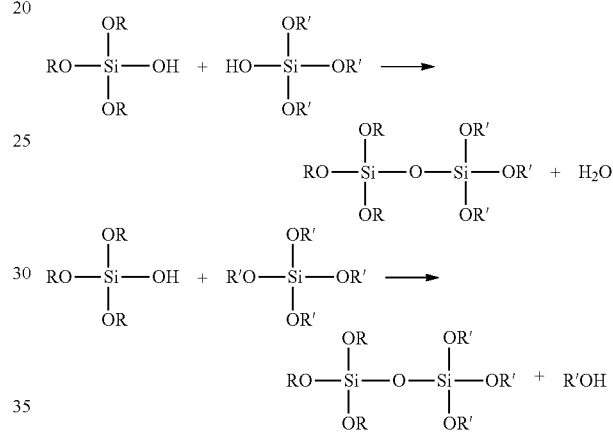

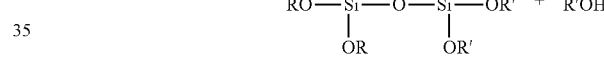

Figure 3:
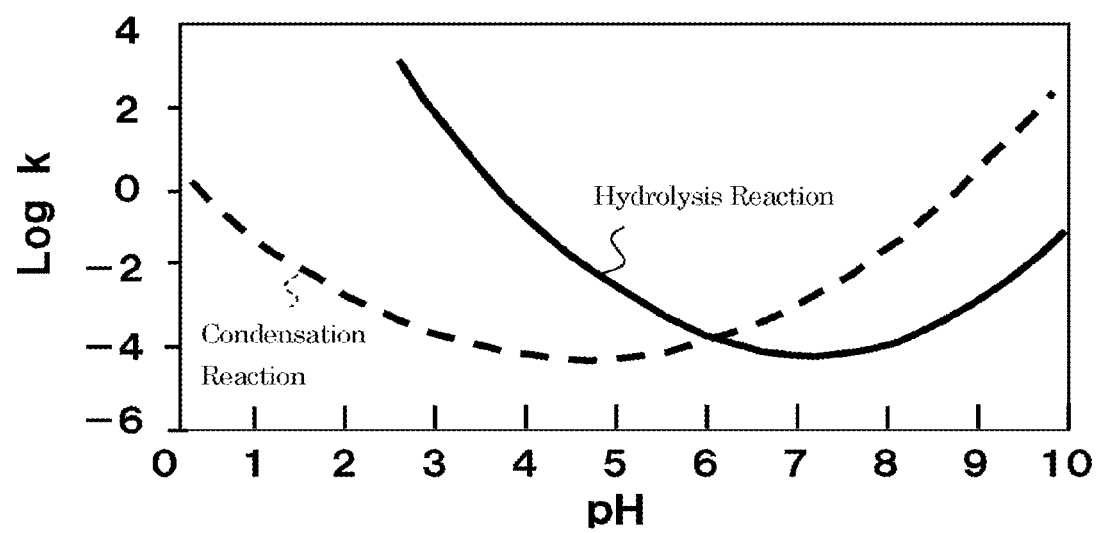
FIG. 3 is a schematic view showing a condensation reaction rate and a hydrolysis reaction rate in a sol-gel reaction using a tetraalkoxysilane (TEOS).

In the step (1), the initial pH value of the emulsion obtained by emulsifying the organic phase including the at least one organic compound and the tetraalkoxysilane in the water phase including the surfactant (i.e., the initial pH value in the sol-gel reaction of the step (1)) is maintained higher than the initial pH value in the sol-gel reaction of the below-mentioned step (2) under acidic conditions, so that as shown in FIG. 3, the hydrolysis reaction is allowed to proceed relatively predominantly over the condensation reaction. Therefore, it is considered that by maintaining the initial pH value in the sol-gel reaction of the step (1) in the aforementioned specific range under acidic conditions, and controlling the amount of the tetraalkoxysilane used therein to the range of not less than 10% by mass and not more than 60% by mass on the basis of the organic compound, the first shell is formed as a thin film having a high density which is constituted of a uniform silica crosslinked product.

On the other hand, the amount of the tetraalkoxysilane used in the step (2) is preferably not less than 10% by mass, and more preferably not less than 15% by mass, and is also preferably not more than 40% by mass, and more preferably not more than 30% by mass on the basis of the organic compound.

The tetraalkoxysilane used in the step (2) is preferably a tetraalkoxysilane containing an alkoxy group having 1 to 3 carbon atoms, and more preferably tetraethoxysilane (hereinafter also referred to as "TEOS"), from the viewpoint of promoting the sol-gel reaction.

The initial pH value in the sol-gel reaction of the step (2) is maintained below the initial pH value in the sol-gel reaction of the step (1). More specifically, the initial pH value in the sol-gel reaction of the step (2) is preferably not less than 2.5, and more preferably not less than 2.9, and is also preferably less than 3.5, more preferably not more than 3.4, and even more preferably not more than 3.3.

In the step (2), when the sol-gel reaction is allowed to proceed while maintaining the initial pH value of the water dispersion (hereinafter also referred to as a "suspension") containing the capsules obtained in the step (1) (i.e., the initial pH value in the sol-gel reaction of the step (2)) below the initial pH value in the sol-gel reaction of the aforementioned step (1) under acidic conditions and adding dropwise the tetraalkoxysilane thereto, as shown in FIG. 3, it is possible to allow the hydrolysis reaction to proceed predominantly and then allow the condensation reaction to proceed while preventing aggregation of the capsules. Therefore, it is considered that by maintaining the initial pH value in the sol-gel reaction of the step (2) in the aforementioned specific range under acidic conditions, and controlling the amount of the tetraalkoxysilane added to the suspension to the range of not less than 10% by mass and not more than 40% by mass on the basis of the organic compound, in particular, adding dropwise the tetraalkoxysilane to the suspension over a period of not less than 10 min and not more than 1,000 min, it is possible to suitably control a concentration of a silica sol that is produced by hydrolysis of the tetraalkoxysilane in the reaction system, and efficiently deposit and condense the silica sol on the first shell, so that the second shell has a higher-order structure in which silica is present not only in the direction along an interface between the first and second shells but also in the thickness direction thereof, then, is formed into a mesoporous structure.

In the process for producing the microcapsules according to the present invention, the total amount of the tetraalkoxysilane used therein is preferably not less than 20% by mass, and more preferably not less than 30% by mass, and is also preferably not more than 60% by mass, and more preferably not more than 50% by mass on the basis of the organic compound. When controlling the total amount of the tetraalkoxysilane used in the production process to the above specific range, it is possible to retain the organic compound in the core over a long period of time.

In the step (1), the microcapsules each including the core and the first shell are produced. In the step (1), the organic phase containing the at least one organic compound and the tetraalkoxysilane is emulsified in the water phase containing the surfactant to prepare an emulsion. The pH value of the resulting emulsion (i.e., the initial pH value in the sol-gel reaction of the step (1)) is preferably controlled to not less than 3.5, and more preferably not less than 4.3, using an acid solution or an alkaline solution, and the solution obtained after controlling a pH value thereof is stirred at a temperature of preferably not lower than 5° C., more preferably not lower than 10° C., and even more preferably not lower than 15° C., and also preferably not higher than 70° C., more preferably not higher than 50° C., and even more preferably not higher than 40° C. for a predetermined period of time (for example, not less than 5 h and not more than 48 h) to obtain the microcapsules each including the first shell encapsulating the core including the organic compound.

Examples of the acid solution used in the step (1) include solutions prepared by adding an inorganic acid such as hydrochloric acid, nitric acid, sulfuric acid and phosphoric acid; an organic acid such as acetic acid and citric acid; a cation exchange resin, or the like, to water or ethanol, etc. Of these acid solutions, particularly preferred is a solution containing hydrochloric acid or citric acid. Examples of the alkaline solution used in the step (1) include a sodium hydroxide solution, a sodium hydrogen carbonate solution, a potassium hydroxide solution, an ammonium hydroxide solution and the like. Of these alkaline solutions, particularly preferred are a sodium hydroxide solution and a sodium hydrogen carbonate solution.

<Step (1-1)>

The process for producing microcapsules according to the present invention may further include the following step (1-1):

step (1-1): prior to the step (2), adding a cationic polymer compound to the water dispersion containing the capsules obtained in the step (1).

When conducting the step (1-1) of adding the cationic polymer compound, it is possible to enhance cationic properties of a surface of the respective capsules, promote adsorption of the tetraalkoxysilane added in the next step (2) onto the capsules, and enhance retentivity of the materials to be encapsulated in the capsules. Further, by conducting the step (1-1), it is possible to relieve such a condition that the capsules obtained in the step (1) are likely to be aggregated in the water dispersion (suspension), and suppress formation of coarse particles, etc., in the subsequent step (2).

As the cationic polymer compound, there may be used not only a quaternary ammonium salt group-containing polymer compound, but also a nitrogen-based cationic group-containing polymer compound and a polymer compound capable of exhibiting cationic properties by controlling a pH value thereof.

The equivalent amount of the cationic group in the cationic polymer compound is preferably not less than 1 meq/g, more preferably not less than 3 meq/g, and even more preferably not less than 4.5 meq/g, from the viewpoints of attaining good dispersibility of the capsules and suppressing formation of coarse particles, and enhancing retentivity of the materials to be encapsulated in the capsules. Also, from the same viewpoints, the equivalent amount of the cationic group in the cationic polymer compound is preferably not more than 10 meq/g, and more preferably not more than 8 meq/g. The cationic polymer compound may also contain an anionic group therein. In this case, the equivalent amount of the anionic group in the cationic polymer compound is preferably not more than 3.5 meq/g, more preferably not more than 2 meq/g, and even more preferably not more than 1 meq/g. Meanwhile, in the present invention, the equivalent amount of the cationic group in the cationic polymer compound as used herein means the value calculated on the basis of the monomer composition.

Specific examples of the cationic polymer compound include polydiallyldimethylammonium chlorides and copolymers thereof such as poly(diallyldimethylammonium chloride), poly(acrylic acid-co-diallyldimethylammonium chloride), poly(acrylamide-co-diallyldimethylammonium chloride) and poly(acrylamide-co-acrylic acid-co-diallyldimethylammonium chloride), poly(2-(methacryloyloxy) ethyltrimethylammonium chloride), polyethyleneimine, polyallylamine, cationized cellulose, cationized guar gum, cationized tara gum, cationized fenugreek gum and cationized locust bean gum. Of these cationic polymer compounds, preferred are polydiallyldimethylammonium chlorides and copolymers thereof, more preferred is at least one compound selected from the group consisting of poly(diallyldimethylammonium chloride), poly(acrylic acid-co-diallyldimethylammonium chloride) and poly(acrylamide-coacrylic acid-co-diallyldimethylammonium chloride), and even more preferred is poly(diallyldimethylammonium chloride).

The amount of the cationic polymer compound added is preferably not less than 0.05% by mass, more preferably not less than 0.1% by mass, and even more preferably not less than 0.2% by mass, and is also preferably not more than 5% by mass, more preferably not more than 3% by mass, and even more preferably not more than 1% by mass, on the basis of the organic compound to be encapsulated in the capsules.

<Step (2)>

In the step (2), the microcapsules each further including the second shell contacting the first shell are formed.

In the step (2), the water dispersion (suspension) containing the microcapsules in which the first shell is formed is preferably controlled to a temperature of not lower than 5° C., more preferably not lower than 10° C., and even more preferably not lower than 15° C., and also preferably not higher than 70° C., more preferably not higher than 50° C., and even more preferably not higher than 40° C., and further the pH value of the suspension (i.e., the initial pH value in the sol-gel reaction of the step (2)) is controlled to the range of not less than 2.5 and less than 3.5 using an acid solution or an alkaline solution. Next, the tetraalkoxysilane is added to the thus pH-controlled suspension, in particular, added dropwise thereto over a predetermined period of time. After completion of adding dropwise a whole amount of the tetraalkoxysilane, the resulting mixture is stirred for a predetermined period of time and then cooled to obtain the microcapsules that each include the core including the organic compound, the first shell, and the second shell formed on the first shell.

As the acid solution used in the step (2), there may be mentioned solutions prepared by adding an inorganic acid such as hydrochloric acid, nitric acid and sulfuric acid; an organic acid such as acetic acid and citric acid; a cation exchange resin, or the like, to water or ethanol. Of these acid solutions, particularly preferred is a solution containing hydrochloric acid or citric acid. Examples of the alkaline solution used in the step (2) include a sodium hydroxide solution, a sodium hydrogen carbonate solution, a potassium hydroxide solution, an ammonium hydroxide solution and the like. Of these alkaline solutions, particularly preferred are a sodium hydroxide solution and a sodium hydrogen carbonate solution.

The time of the dropwise addition of the tetraalkoxysilane in the step (2) is preferably not less than 10 min, more preferably not less than 60 min, and even more preferably not less than 100 min, and is also preferably not more than 1,000 min, more preferably not more than 700 min, and even more preferably not more than 500 min.

The microcapsules obtained in the step (2) are in the form of a dispersion of the microcapsules in water. The resulting dispersion may be directly used as such, in the aimed applications. However, in some cases, the microcapsules may be separated from the dispersion upon use. As the separating method, there may be used a filtration method, a centrifugal separation method, etc.

<Step (3)>

The process for producing microcapsules according to the present invention may further include the following step (3):

step (3): mixing a dispersion containing the capsules obtained in the step (2) and an organic polymer compound aqueous solution to form capsules including a third shell.

The organic polymer compound used in the step (3) is preferably at least one organic polymer compound selected from the group consisting of a water-soluble synthetic polymer compound and a natural polymer compound.

The dispersion containing the microcapsules obtained in the step (2) is dispersed in the organic polymer compound aqueous solution to obtain a microcapsule composition including the third shell.

The water-soluble synthetic polymer compound is preferably an anionic synthetic polymer compound.

The anionic synthetic polymer compound is preferably in the form of a copolymer of a hydrophobic monomer and a carboxy group-containing monomer. The copolymer of the hydrophobic monomer and the carboxy group-containing monomer is preferably an isobutylene-maleic acid copolymer or a styrene-maleic acid copolymer.

Examples of the preferred natural polymer compound include homopolysaccharides, heteropolysaccharides, mucopolysaccharides, chitin, chitosan, gum arabic, sodium alginate, gelatin, xanthan gum, carageenan, agar, curdlan and gellan gum, as well as polymer compounds obtained by modifying these compounds.

Of these natural polymer compounds, gum arabic or gelatin is preferred.

In the step (3), the third shell formed of the organic polymer compound is formed on the respective microcapsules including the second shell which are obtained in the step (2). As a result of conducting the step (3), it is possible to obtain the microcapsules each containing the core formed of the at least one organic compound, the first shell including silica as a constitutional component thereof which is contacted with the core, the second shell including silica as a constitutional component thereof which is contacted with the first shell, and the third shell that is contacted with the second shell and formed of the organic polymer compound.

[Microcapsules]

The microcapsules according to the present invention each include a core formed of at least one organic compound, a first shell encapsulating the core, and a second shell encapsulating the first shell, in which the first shell encapsulating the core includes silica as a constitutional component thereof and has a thickness of not less than 5 nm and not more than 20 nm; the second shell encapsulating the first shell includes silica as a constitutional component thereof and has a thickness of not less than 10 nm and not more than 100 nm; and the microcapsules have an average particle size of not less than 0.5 µm and not more than 50 µm.

Furthermore, the microcapsules according to the present invention may also each include a third shell formed of an organic polymer compound which is contacted with the second shell.

The reason why the microcapsules according to the present invention are capable of retaining an organic compound as an active ingredient such as fragrance materials therein over a long period of time is considered as follows, though it is not clearly determined.

That is, in the microcapsules according to the present invention, it is considered that in the step (1) of the aforementioned production process, by maintaining the initial pH value of the emulsion obtained by emulsifying the organic phase containing the at least one organic compound and the tetraalkoxysilane in the water phase containing the surfactant higher than the initial pH value in the sol-gel reaction of the below-mentioned step (2) under acidic conditions (for example, maintaining the initial pH value of the emulsion in the range of not less than 3.5 and not more than 4.3) and controlling an amount of the tetraalkoxysilane used therein to the range of not less than 10% by mass and not more than 60% by mass on the basis of the organic compound, it is possible to form the first shell as a dense layer having a high density which is formed of a uniform silica crosslinked product. As a result, it is suggested that the organic compound encapsulated in the first shell can be retained over a longer period of time as compared to those shells obtained by the conventional production processes.

In addition, in the step (2) of the aforementioned production process, it is considered that by maintaining the initial pH value of the suspension obtained in the step (1) below the initial pH value in the sol-gel reaction of the step (1) under acidic conditions (for example, maintaining the initial pH value of the suspension in the range of not less than 2.5 and less than 3.5) and controlling an amount of the tetraalkoxysilane to be added dropwise to the suspension to the range of not less than 10% by mass and not more than 40% by mass on the basis of the organic compound, the second shell has a higher-order structure in which silica is present not only in the direction along an interface between the first and second shells but also in the thickness direction thereof, i.e., is formed into a mesoporous structure having a pore size of more than 2 nm and not more than 50 nm. Also, it is considered that the mesoporous structure of the second shell serves for not only further improving retentivity of the organic compound encapsulated in the microcapsules, but also enhancing strength of the microcapsules against a pressure exerted from outside of the microcapsules as compared to the capsules obtained by the conventional methods.

Furthermore, it is considered that the two-layer shell structure constituted of the aforementioned first and second shells serves for enhancing denseness of an entire portion of the shells in the microcapsules as compared to the capsules obtained by the conventional methods.

Thus, as a result of combination of the aforementioned advantages of the microcapsules according to the present invention, it is considered that the organic compound as an active ingredient such as fragrance materials can be retained therein over a long period of time.

The silica constituting the first and second shells in the microcapsules according to the present invention may be produced from a silica source such as an alkoxysilane which is capable of producing a silanol compound by hydrolysis thereof. More specifically, the silica source includes compounds represented by the following general formula (1):

$$SiY_4 \tag{1}$$

wherein Y is a monovalent hydrolysable group capable of being hydrolyzed into a hydroxy group.

In the general formula (1), Y is preferably an alkoxy group having 1 to 4 carbon atoms, more preferably an alkoxy group having 1 to 3 carbon atoms, even more preferably a methoxy group or an ethoxy group, and further even more preferably an alkoxy group having 2 carbon atoms.

Of these silica sources, preferred is tetraethoxysilane (TEOS).

The thickness of the first shell is preferably not less than 5 nm, and is also preferably not more than 20 nm, and more preferably not more than 15 nm. In addition, the first shell is preferably in the form of a dense layer in which pores are present in as small an amount as possible, in order to retain the organic compound encapsulated in the microcapsules over a long period of time.

As described above, the thickness of the second shell is preferably not less than 10 nm, and more preferably not less than 20 nm, and is also preferably not more than 100 nm, and more preferably not more than 80 nm. In addition, the second shell has a mesoporous structure as a higher-order structure in which silica is present not only in the direction along an interface between the first and second shells but also in the thickness direction thereof.

The "mesoporous structure" of the second shell as used herein means such a structure that the size of pores (i.e., so-called mesopores) present therein is preferably more than 2 nm, more preferably not less than 10 nm, and even more preferably not less than 30 nm, and is also preferably not more than 50 nm, more preferably not more than 45 nm, and even more preferably not more than 40 nm.

The mesoporous structure of the second shell serves for enhancing strength of the resulting microcapsules as compared to the capsules obtained by the conventional methods.

The average particle size of the microcapsules according to the present invention is not less than 0.5 µm, preferably not less than 0.7 µm, and more preferably not less than 1 µm, and is also not more than 50 µm, preferably not more than 10 µm, and more preferably not more than 5 µm. When the average particle size of the microcapsules is less than 0.5 µm, the effects of the components contained in the core tends to be hardly exhibited owing to a less amount of the materials constituting the core, and the retentivity of the organic compound encapsulated in the microcapsules tends to be deteriorated owing to increase in specific surface area of the capsules. On the other hand, when the average particle size of the microcapsules is more than 50 µm, the resulting microcapsules tend to be deteriorated in physical strength, so that the retentivity of the organic compound encapsulated therein tends to be deteriorated.

Meanwhile, in the present invention, the average particle size of the microcapsules may be measured using a laser diffraction/scattering particle size distribution analyzer "LA-950" (tradename) available from Horiba Ltd. In this case, the measurement is carried out by using a flow cell and water as a medium, and setting a refractive index of the medium to 1.40-0i. In the measurement, a dispersion containing the microcapsules is added to the flow cell, and the particle sizes thereof are measured at a concentration at which a transmittance of the dispersion is near 90% to determine a volume-based average particle size of the microcapsules.

The average thicknesses of the first and second shells in the microcapsules as well as the pore sizes in the first and second shells are measured by observation using a transmission electron microscope (TEM). More specifically, under the observation using a transmission electron microscope, the thicknesses of the first and second shells as well as the pore sizes in the first and second shells are actually measured on a micrograph obtained therefrom. The measurement procedure is repeated 5 times while varying a field of view therefor. The thus obtained measurement data are used to determine thicknesses of the first and second shells and distribution of the pore sizes in the first and second shells. The magnification of the transmission electron microscope is usually from 10,000 to 100,000 times as a scale, but may be adequately adjusted according to the size of the microcapsules to be measured. In this case, as the transmission electron microscope (TEM), there may be used, for example, "JEM-2100" (tradename) available from JEOL Ltd.

With respect to the aforementioned embodiments, the present invention further provides the following aspects relating to the process for producing microcapsules, and the microcapsules.

<1> A process for producing microcapsules each containing a first shell and a second shell which include silica as a constitutional component thereof, and a core including at least one organic compound which is encapsulated within the first shell, said process including the following steps (1) and (2):

step (1); emulsifying an organic phase including the at least one organic compound and a tetraalkoxysilane such that a content of the tetraalkoxysilane in the organic phase is not less than 10% by mass and not more than 60% by mass on the basis of the organic compound, in a water phase including a surfactant, and subjecting the resulting emulsion to sol-gel reaction under acidic conditions to form capsules each including the core and the first shell; and step (2): further adding a tetraalkoxysilane to a water dispersion containing the capsules obtained in the step (1), and subjecting the obtained mixture to sol-gel reaction while maintaining an initial pH value in the sol-gel reaction of the step (2) below an initial pH value in the sol-gel reaction of the step (1) to form the capsules each including the second shell encapsulating the first shell.

<2> The process for producing microcapsules according to the aspect <1>, wherein the initial pH value in the sol-gel reaction of the step (1) is preferably not less than 3.5, and more preferably not less than 3.7, and is also preferably not more than 4.3, and more preferably not more than 3.9.

<3> The process for producing microcapsules according to the aspect <1> or <2>, wherein the initial pH value in the sol-gel reaction of the step (2) is preferably not less than 2.5, and more preferably not less than 2.9, and is also preferably less than 3.5, more preferably not more than 3.4, and even more preferably not more than 3.3.

<4> The process for producing microcapsules according to any one of the aspects <1> to <3>, wherein the alkoxy group of the tetraalkoxysilane is preferably an alkoxy group having 1 to 3 carbon atoms, more preferably a methoxy group or an ethoxy group, and even more preferably an ethoxy group, and the tetraalkoxysilane is particularly preferably tetraethoxysilane.

<5> The process for producing microcapsules according to any one of the aspects <1> to <4>, wherein an amount of the tetraalkoxysilane used in the step (1) is preferably not less than 12% by mass, and more preferably not less than 14% by mass, and is also preferably not more than 50% by mass, more preferably not more than 40% by mass, and even more preferably not more than 35% by mass, on the basis of the organic compound.

<6> The process for producing microcapsules according to any one of the aspects <1> to <5>, wherein an amount of the tetraalkoxysilane used in the step (2) is preferably not less than 10% by mass, and more preferably not less than 15% by mass, and is also preferably not more than 40% by mass, and more preferably not more than 30% by mass, on the basis of the organic compound.

<7> The process for producing microcapsules according to any one of the aspects <1> to <6>, wherein a total amount of the tetraalkoxysilane used in the process is preferably not less than 20% by mass, and more preferably not less than 30% by mass, and is also preferably not more than 60% by mass, and more preferably not more than 50% by mass, on the basis of the organic compound.

<8> The process for producing microcapsules according to any one of the aspects <1> to <7>, wherein the organic compound contained in the core is preferably at least one material selected from the group consisting of a fragrance material, a fragrance precursor, an oil, an antioxidant, a cooling agent, a dye, a pigment, a silicone, a solvent and an oil-soluble polymer, more preferably at least one material selected from the group consisting of a fragrance material, a fragrance precursor, an oil, an antioxidant and a solvent, even more preferably at least one material selected from the group consisting of a fragrance material and a fragrance precursor, and further even more preferably a fragrance precursor.

<9> The process for producing microcapsules according to the aspect <8>, wherein the fragrance precursor is a compound or the like which is capable of releasing fragrance components by reacting with water, preferably at least one compound selected from the group consisting of a silicic acid ester compound containing an alkoxy component derived from a fragrance alcohol, a fatty acid ester compound containing an alkoxy component derived from a fragrance alcohol, an acetal compound or a hemiacetal compound obtained by the reaction between a carbonyl component derived from a fragrance aldehyde or a fragrance ketone and an alcohol compound, a shiff base compound obtained by the reaction between a carbonyl component derived from a fragrance aldehyde or a fragrance ketone and a primary amine compound, and a hemiaminal compound or a hydrazone compound obtained by the reaction between a carbonyl component derived from a fragrance aldehyde or a fragrance ketone and a hydrazine compound, and more preferably a silicic acid ester compound containing an alkoxy component derived from a fragrance alcohol.

<10> The process for producing microcapsules according to the aspect <8>, wherein the fragrance precursor is a compound capable of releasing fragrance components by reacting with light, and preferably at least one compound selected from the group consisting of a 2-nitrobenzyl ether compound containing an alkoxy component derived from a fragrance alcohol, an α-ketoester compound containing a carbonyl component derived from a fragrance aldehyde or a fragrance ketone, and a coumalic acid ester compound containing an alkoxy component derived from a fragrance alcohol.

<11> The process for producing microcapsules according to any one of the aspects <1> to <10>, wherein a ClogP value of the organic compound is preferably not less than 2, more preferably not less than 3, and even more preferably not less than 4, and is also preferably not more than 30, more preferably not more than 20, and even more preferably not more than 10.

<12> The process for producing microcapsules according to any one of the aspects <1> to <11>, wherein the surfactant used in the step (1) is preferably a cationic surfactant.

<13> The process for producing microcapsules according to the aspect <12>, wherein the cationic surfactant is a quaternary ammonium salt, a nitrogen-based cationic group-containing compound or a surfactant capable of exhibiting cationic properties by controlling a pH value thereof, and preferably an alkylamine salt or a quaternary ammonium salt, in which the number of carbon atoms in the alkyl group is preferably from 10 to 22, more preferably from 12 to 20, and even more preferably from 14 to 18.

<14> The process for producing microcapsules according to the aspect <13>, wherein the alkylamine salt is at least one compound selected from the group consisting of laurylamine acetate and stearylamine acetate, and the quaternary ammonium salt is at least one compound selected from the group consisting of alkyltrimethylammonium chlorides such as lauryltrimethylammonium chloride, stearyltrimethylammonium chloride and cetyltrimethylammonium chloride, dialkyldimethylammonium chlorides such as distearyldimethylammonium chloride, and alkylbenzyldimethylammonium chlorides.

<15> The process for producing microcapsules according to the aspect <13>, wherein the cationic surfactant is a quaternary ammonium salt.

<16> The process for producing microcapsules according to any one of the aspects <1> to <15>, wherein in the step (1), a solution obtained after controlling a pH value thereof is stirred at a temperature of preferably not lower than 5° C., more preferably not lower than 10° C., and even more preferably not lower than 15° C., and also preferably not higher than 70° C., more preferably not higher than 50° C., and even more preferably not higher than 40° C. for a predetermined period of time (for example, not less than 5 h and not more than 48 h) to obtain the microcapsules each including the first shell encapsulating the core including the organic compound.

<17> The process for producing microcapsules according to any one of the aspects <1> to <16>, wherein the acid solution used in the step (1) is at least one solution prepared by adding at least one inorganic acid selected from the group consisting of hydrochloric acid, nitric acid, sulfuric acid and phosphoric acid; at least one organic acid selected from the group consisting of acetic acid and citric acid; or a cation exchange resin to water or ethanol, and particularly preferably a solution containing hydrochloric acid or citric acid.

<18> The process for producing microcapsules according to any one of the aspects <1> to <16>, wherein the alkaline solution used in the step (1) is at least one solution selected from the group consisting of a sodium hydroxide solution, a sodium hydrogen carbonate solution, a potassium hydroxide solution and an ammonium hydroxide solution, and particularly preferably a sodium hydroxide solution or a sodium hydrogen carbonate solution.

<19> The process for producing microcapsules according to any one of the aspects <1> to <18>, wherein in the step (2), the water dispersion containing the microcapsules in which the first shell is formed is preferably controlled to a temperature of not lower than 5° C., more preferably not lower than 10° C., and even more preferably not lower than 15° C., and also preferably not higher than 70° C., more preferably not higher than 50° C., and even more preferably not higher than 40° C.

<20> The process for producing microcapsules according to any one of the aspects <1> to <19>, wherein the acid solution used in the step (2) is at least one solution prepared by adding at least one inorganic acid selected from the group consisting of hydrochloric acid, nitric acid and sulfuric acid; at least one organic acid selected from the group consisting of acetic acid and citric acid; or a cation exchange resin to water or ethanol, and particularly preferably a solution containing hydrochloric acid or citric acid.

<21> The process for producing microcapsules according to any one of the aspects <1> to <19>, wherein the alkaline solution used in the step (2) is at least one solution selected from the group consisting of a sodium hydroxide solution, a sodium hydrogen carbonate solution, a potassium hydroxide solution and an ammonium hydroxide solution, and particularly preferably a sodium hydroxide solution or a sodium hydrogen carbonate solution.

<22> The process for producing microcapsules according to any one of the aspects <1> to <21>, wherein the microcapsules obtained in the step (2) are separated from a water dispersion thereof by a filtration method or a centrifugal separation method.

<23> The process for producing microcapsules according to any one of the aspects <1> to <22>, wherein the tetraalkoxysilane is added dropwise in the step (2), and a time of the dropwise addition of the tetraalkoxysilane in the step (2) is preferably not less than 10 min, more preferably not less than 60 min, and even more preferably not less than 100 min, and is also preferably not more than 1,000 min, more preferably not more than 700 min, and even more preferably not more than 500 min.

<24> The process for producing microcapsules according to any one of the aspects <1> to <23>, further including the following step (3):

step (3): mixing a dispersion comprising the capsules obtained in the step (2) and an organic polymer compound aqueous solution to form capsules including a third shell.

<25> The process for producing microcapsules according to the aspect <24>, wherein the organic polymer compound is at least one compound selected from the group consisting of a water-soluble synthetic polymer compound and a natural polymer compound.

<26> The process for producing microcapsules according to the aspect <25>, wherein the water-soluble synthetic polymer compound is an anionic synthetic polymer compound.

<27> The process for producing microcapsules according to the aspect <26>, wherein the anionic synthetic polymer compound is in the form of a copolymer of a hydrophobic monomer and a carboxy group-containing monomer.

<28> The process for producing microcapsules according to the aspect <27>, wherein the copolymer of the hydrophobic monomer and the carboxy group-containing monomer is an isobutylene-maleic acid copolymer or a styrene-maleic acid copolymer.

<29> The process for producing microcapsules according to the aspect <25>, wherein the natural polymer compound is at least one compound selected from the group consisting of homopolysaccharides, heteropolysaccharides, mucopolysaccharides, chitin, chitosan, gum arabic, sodium alginate, gelatin, xanthan gum, carageenan, agar, curdlan and gellan gum, as well as polymer compounds obtained by modifying these compounds.

<30> The process for producing microcapsules according to the aspect <25>, wherein the natural polymer compound is gum arabic or gelatin.

<31> The process for producing microcapsules according to any one of the aspects <1> to <30>, further including the following step (1-1):

step (1-1); prior to the step (2), adding a cationic polymer compound to the water dispersion containing the capsules obtained in the step (1).

<32> The process for producing microcapsules according to the aspect <31>, wherein an equivalent amount of a cationic group in the cationic polymer compound is preferably not less than 1 meq/g, more preferably not less than 3 meq/g, and even more preferably not less than 4.5 meq/g, and is also preferably not more than 10 meq/g, and more preferably not more than 8 meq/g.

<33> The process for producing microcapsules according to the aspect <31> or <32>, wherein the cationic polymer compound contains an anionic group, and an equivalent amount of the anionic group in the cationic polymer compound is preferably not more than 3.5 meq/g, more preferably not more than 2 meq/g, and even more preferably not more than 1 meq/g.

<34> The process for producing microcapsules according to any one of the aspects <31> to <33>, wherein the cationic polymer compound is preferably at least one compound selected from the group consisting of polydiallyldimethylammonium chlorides and copolymers thereof such as poly(diallyldimethylammonium chloride), poly(acrylic acid-co-diallyldimethylammonium chloride), poly(acrylamide-co-diallyldimethylammonium chloride) and poly(acrylamide-co-acrylic acid-co-diallyldimethylammonium chloride), poly(2-(methacryloyloxy) ethyltrimethylammonium chloride), polyethyleneimine, polyallylamine, cationized cellulose, cationized guar gum, cationized tara gum, cationized fenugreek gum and cationized locust bean gum; more preferably at least one compound selected from the group consisting of polydiallyldimethylammonium chlorides and copolymers thereof; even more preferably at least one compound selected from the group consisting of poly(diallyldimethylammonium chloride), poly(acrylic acid-co-diallyldimethylammonium chloride) and poly(acrylamide-co-acrylic acid-co-diallyldimethylammonium chloride); and further even more preferably poly(diallyldimethylammonium chloride).

<35> The process for producing microcapsules according to any one of the aspects <31> to <34>, wherein an amount of the cationic polymer compound added is preferably not less than 0.05% by mass, more preferably not less than 0.1% by mass, and even more preferably not less than 0.2% by mass, and is also preferably not more than 5% by mass, more preferably not more than 3% by mass, and even more preferably not more than 1% by mass, on the basis of the organic compound.

<36> Microcapsules each containing a core including at least one organic compound, a first shell encapsulating the core, and a second shell encapsulating the first shell, in which the first shell encapsulating the core includes silica as a constitutional component thereof and has a thickness of not less than 5 nm and not more than 20 nm; the second shell encapsulating the first shell includes silica as a constitutional component thereof and has a thickness of not less than 10 nm and not more than 100 nm; and the microcapsules have an average particle size of not less than 0.5 μm and not more than 50 μm.

<37> The microcapsules according to the aspect <36>, further containing a third shell formed in contact with the second shell which includes an organic polymer compound.

<38> The microcapsules according to the aspect <37>, wherein the organic polymer compound is at least one organic polymer compound selected from the group consisting of a water-soluble synthetic polymer compound and a natural polymer compound.

<39> Microcapsules produced by the process for producing microcapsules according to any one of the aspects <1> to <35>, each containing a core including at least one organic compound, a first shell encapsulating the core and including silica as a constitutional component thereof, and a second shell encapsulating the first shell and including silica as a constitutional component thereof, in which the microcapsules have an average particle size of not less than 0.5 μm and not more than 50 μm.

<40> The microcapsules according to the aspect <39>, wherein the second shell has a microporous structure.

<41> Microcapsules produced by the process for producing microcapsules according to the aspect <24>, each containing a core including at least one organic compound, a first shell contacting the core and including silica as a constitutional component thereof, a second shell contacting the first shell and including silica as a constitutional component thereof, and a third shell contacting the second shell and including an organic polymer compound.

<42> The microcapsules according to any one of the aspects <36> to <41>, wherein an average particle size of the microcapsules is not less than 0.5 μm, preferably not less than 0.7 μm, and more preferably not less than 1 μm, and is also not more than 50 μm, preferably not more than 10 μm, and more preferably not more than 5 μm.

<43> The microcapsules according to any one of the aspects <36> to <42>, wherein a thickness of the first shell is not less than 5 nm, and is also not more than 20 nm, and preferably not more than 15 nm.

<44> The microcapsules according to any one of the aspects <36> to <43>, wherein a thickness of the second shell is preferably not less than 10 nm, and more preferably not less than 20 nm, and is also preferably not more than 100 nm, and more preferably not more than 80 nm.

EXAMPLES

Various properties of the microcapsules obtained in the following Examples and Comparative Examples were measured by the following methods.

(i) Average Particle Size

The average particle size of the microcapsules was measured using a laser diffraction/scattering particle size distribution analyzer "LA-950" (tradename) available from Horiba, Ltd. The measurement was carried out by using a flow cell and water as a medium, and setting a refractive index of the medium to 1.40-0i. In the measurement, a dispersion containing the microcapsules was added into the flow cell, and the particle sizes thereof were measured at a concentration at which a transmittance of the dispersion was near 90% to determine a volume-based average particle size of the microcapsules.

(ii) Encapsulation Rate of Fragrance Materials within Microcapsules

The dispersion obtained in the step (2) was weighed in an amount of 0.05 g and dispersed in 10 mL of acetonitrile containing 100 μg/mL of dodecane as an internal standard. Then, the resulting solution was irradiated with ultrasonic waves for 10 min, and allowed to pass through a membrane filter "DISMIC(R)-13JP020AN" available from Toyo Roshi Kaisha, Ltd., one more time. The obtained solution was subjected to gas chromatography to measure an amount of fragrance materials contained in the solution and thereby determine an amount of the fragrance components contained in the dispersion.

On the other hand, 0.05 g of the dispersion obtained in the step (2) was allowed to pass through a membrane filter "OMNIPORE; Model No. JAWP04700" available from MILLIPORE to recover the capsules on the membrane filter. Further, the thus recovered capsules were rinsed on the membrane filter with 10 mL of ion-exchanged water and then with 10 mL of hexane. Thereafter, the capsules were dipped in 10 mL of acetonitrile containing 100 μg/mL of dodecane as an internal standard. The resulting solution was irradiated with ultrasonic waves for 10 min, and allowed to pass through a membrane filter "DISMIC(R)-13JP020AN" available from Toyo Roshi Kaisha, Ltd., one more time. Then, the obtained solution was subjected to gas chromatography to measure an amount of fragrance materials contained in the solution and thereby determine an amount of the fragrance components encapsulated in the capsules.

The encapsulation rate (%) of the fragrance materials was calculated from the amount of the fragrance components contained in the above-obtained dispersion and the amount of the fragrance components encapsulated in the capsules according to the following formula.

> Encapsulation Rate (%) of Fragrance Materials=[Amount of Fragrance Components Encapsulated in Capsules]/[Amount of Fragrance Components Contained in Dispersion]×100

(iii) Evaluation of Long-Term Storage Stability of Fragrance Materials within Microcapsules in Softener The respective microcapsule suspensions and dispersions obtained in the below-mentioned Examples and Comparative Examples were weighed in an amount of 0.28 g, and added and dispersed in 4.72 g of a commercially available softener "FLAIR FRAGRANCE" (tradename) available from Kao Corporation to prepare a suspension.

The softener containing the microcapsule dispersion was put in a screw vial and hermetically sealed therein, and stored at 40° C.

Immediately after blending these materials as well as after the elapse of 2 days and 24days from the blending, the screw vial was taken out, and 0.2 g of the softener was sampled using a pipette, and diluted with 200 g of a 0.2% cyclohexanol aqueous solution. The resulting diluted solution was sampled in an amount of 50 g, heated at 50° C. for 15 min, and then allowed to pass through a membrane filter "OMNIPORE; Model No. JAWP04700" available from MILLIPORE to recover the capsules on the membrane filter. Further, the thus recovered capsules were rinsed on the membrane filter with 10 mL of ion-exchanged water and then with 10 mL of hexane. Thereafter, the capsules were dipped in 2mL of acetonitrile containing 20 μg/mL of dodecane as an internal standard and maintained at 50° C. for 20 min to elute the fragrance materials contained in the capsules. The resulting solution was allowed to pass through a membrane filter "DISMIC(R)-13JP020AN" available from Toyo Roshi Kaisha, Ltd., one more time. Then, the obtained solution was subjected to gas chromatography to measure amounts of the respective fragrance materials contained in the solution. The thus measured amounts of the fragrance materials were determined as amounts of the fragrance components encapsulated in the capsules. The retentivity of the fragrance materials was calculated according to the following formula.

> Retentivity (%) of Fragrance Materials={(Amount of Fragrance Components Encapsulated in Capsules after Storage)/(Amount of Fragrance Components Encapsulated in Capsules immediately after Being Blended in Softener)}×100

(iv) Evaluation of Long-Term Storage Stability of Fragrance Materials within Microcapsules in Liquid Detergent The respective microcapsule suspensions and dispersions obtained in the below-mentioned Examples and Comparative Examples were weighed in an amount of 0.28 g, and added and dispersed in 4.72 g of a commercially available liquid detergent "NEWBEADS NEO" (tradename) available from Kao Corporation. The liquid detergent containing the microcapsule dispersion was put in a screw vial and hermetically sealed therein, and stored at 40° C.

Immediately after blending these materials as well as after the elapse of 2 days and any of one week, 2 weeks and 3 weeks from the blending, the screw vial was taken out, and 0.2 g of the liquid detergent was sampled using a pipette, and diluted with 200 g of ion-exchanged water. The resulting diluted solution was sampled in an amount of 50 g, and then allowed to pass through a membrane filter "OMNIPORE; Model No. JAWP04700" available from MILLIPORE to recover the capsules on the membrane filter. Further, the thus recovered capsules were rinsed on the membrane filter with 10 mL of ion-exchanged water and then with 10 mL of hexane. Thereafter, the capsules were dipped in 2 mL of acetonitrile containing 20 μg/mL of dodecane as an internal standard and maintained at 50° C. for 20 min to elute the fragrance materials contained in the capsules. The resulting solution was allowed to pass through a membrane filter "DISMIC(R)-13JP020AN" available from Toyo Roshi Kaisha, Ltd., one more time. Then, the obtained solution was subjected to gas chromatography to measure amounts of the respective fragrance materials contained in the solution. The thus measured amounts of the fragrance materials were determined as amounts of the fragrance components encapsulated in the capsules. The retentivity of the fragrance materials was calculated according to the following formula.

> Retentivity (%) of Fragrance Materials={(Amount of Fragrance Components Encapsulated in Capsules after Storage)/(Amount of Fragrance Components Encapsulated in Capsules immediately after Being Blended in Liquid Detergent)}×100

(v) Evaluation of Long-Term Storage Stability of Silicic Acid Ester within Microcapsules in Hair Shampoo The respective microcapsule suspensions obtained in the below-mentioned Examples and Comparative Examples were weighed in an amount of 0.2 g, and added and dispersed in 7.8 g of a commercially available hair shampoo "ESSENTIAL SHAMPOO" (tradename) available from Kao Corporation. The hair shampoo containing the microcapsule dispersion was put in a screw vial and hermetically sealed therein, and stored at 50° C.

Immediately after blending these materials as well as after the elapse of 3 days and 2 weeks from the blending, the screw vial was taken out, and 0.2 g of the hair shampoo was sampled using a pipette, and diluted with 200 g of ion-exchanged water. The resulting diluted solution was sampled in an amount of 50 g, and then allowed to pass through a membrane filter "OMNIPORE; Model No. JAWP04700" available from MILLIPORE to recover the capsules on the membrane filter. Further, the thus recovered capsules were rinsed on the membrane filter with 10 mL of ion-exchanged water and then with 10 mL of hexane. Thereafter, the capsules were dipped in 2 mL of acetonitrile containing 10 μg/mL of methyl benzoate as an internal standard, followed by irradiating the obtained solution with ultrasonic waves for 30 min to thereby extract the fragrance materials and the silicic acid ester contained in the capsules. The resulting solution was allowed to pass through a membrane filter "DISMIC(R)-13JP020AN" available from Toyo Roshi Kaisha, Ltd., one more time. Then, the obtained solution was subjected to liquid chromatography to measure an amount of the silicic acid ester contained in the solution. The thus measured amount of the silicic acid ester was determined as an amount of the silicic acid ester encapsulated in the capsules. The retentivity of the silicic acid ester was calculated according to the following formula.

> Retentivity (%) of Silicic Acid Ester={(Amount of Silicic Acid Ester Encapsulated in Capsules after Storage)/(Amount of Silicic Acid Ester Encapsulated in Capsules immediately after Being Blended)}×100

(vi) Evaluation of Long-Term Storage Stability of Silicic Acid Ester in Hair Shampoo (Example 9)

The geraniol-substituted silicic acid ester composition synthesized in the below-mentioned Production Example 1 was weighed in an amount of 0.1 g, and added and dispersed in 19.85 g of a commercially available hair shampoo "ESSENTIAL SHAMPOO" (tradename) available from Kao Corporation. The hair shampoo containing the composition was put in a screw vial and hermetically sealed therein, and stored at 50° C.

After the elapse of 3 days and 2 weeks, the screw vial was taken out, and 0.2 g of the hair shampoo was sampled using a pipette, and dipped in 10 mL of acetonitrile containing 10μg/mL of methyl benzoate as an internal standard to thereby extract the fragrance materials and the silicic acid ester contained in the hair shampoo. The resulting solution was allowed to pass through a membrane filter "DISMIC (R)-13JP020AN" available from Toyo Roshi Kaisha, Ltd. Then, the obtained solution was subjected to liquid chromatography to measure an amount of the silicic acid ester contained in the solution. The retentivity of the silicic acid ester was calculated according to the following formula.

Retentivity (%) of Silicic Acid Ester={(Amount of Silicic Acid Ester Contained in Preparation after Storage)/(Amount of Silicic Acid Ester Contained in Preparation when Blended)}×100

<Raw Materials, Etc.>

The respective model fragrance materials having the following compositions shown in Tables 1 to 4 were prepared as models.

TABLE 1

Model Fragrance Material A (Volume-Average cLogP: 4.2; Specific Gravity: 0.96)

| Name of fragrance component | Amount compounded | cLogP |
|---|---|---|
| Hexyl acetate | 10 parts by mass | 2.8 |
| Methyl dihydrojasmonate | 10 parts by mass | 3 |
| Tetrahydrolinalol | 10 parts by mass | 3.6 |
| α-Ionone | 10 parts by mass | 4.3 |
| Lilial | 20 parts by mass | 4.4 |
| Hexylcinnamyl aldehyde | 20 parts by mass | 4.8 |
| Hexyl salicylate | 20 parts by mass | 5.1 |

TABLE 2

Model Fragrance Material B (Volume-Average cLogP: 4.2; Specific Gravity: 0.95)

| Name of fragrance component | Amount compounded | cLogP |
|---|---|---|
| Hexyl acetate | 10 parts by mass | 2.8 |
| Citral | 20 parts by mass | 3.5 |
| Tetrahydrolinalol | 10 parts by mass | 3.6 |
| δ-Damascone | 10 parts by mass | 4.2 |
| Cis-3-hexen-1-yl salicylate | 20 parts by mass | 4.8 |
| Limonene | 10 parts by mass | 4.9 |
| Hexyl salicylate | 20 parts by mass | 5.1 |

TABLE 3

Model Fragrance Material C (Volume-Average cLogP: 4.2; Specific Gravity: 0.95)

| Name of fragrance component | Amount compounded | cLogP |
|---|---|---|
| l-Menthol | 60 parts by mass | 3.4 |
| Hexyl salicylate | 30 parts by mass | 5.1 |
| Isopropyl myristate | 10 parts by mass | 7.2 |

Production Example 1

Synthesis of Geraniol-Substituted Silicic Acid Ester Composition (Molar Ratio of Geraniol to Silicon Atom=4:1) Using Geraniol as Fragrance Alcohol A 300 mL four-necked flask was charged with 62.5 g of (0.30 mol) of tetraethoxysilane, 185.1 g (1.20 mol) of geraniol and 0.39 g of a 5.6% sodium methoxide methanol solution, and the contents of the flask were stirred at 120° C. for 2 h while distilling off ethanol therefrom under nitrogen flow. After 2 h, the pressure within the reaction vessel was gradually decreased up to 8 kPa, and the contents thereof were further stirred at 120° C. for 3 h while distilling off ethanol therefrom, and then cooled, thereby obtaining a geraniol-substituted silicic acid ester composition. The content of the silicic acid ester represented by the formula (1) containing an alkoxy group formed by removing a hydrogen atom from a hydroxy group of geraniol in the thus obtained silicic acid ester composition was 84% by mass.

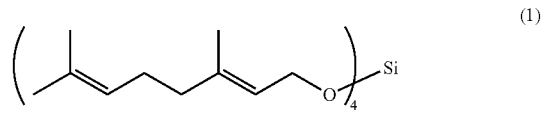

(1)

TABLE 4

Model Fragrance Material D (Volume-Average cLogP: 9.7; Specific Gravity: 0.95)

| Name of fragrance component | Amount compounded | cLogP |
|---|---|---|
| Geraniol-substituted silicic acid ester composition | 50 parts by mass | 14.5 |
| Hexylcinnamyl aldehyde | 50 parts by mass | 4.8 |

<Production of Microcapsules>

Example 1 (Production of Microcapsules Including First Shell and Second Shell)

Step (1)

An aqueous solution was prepared by diluting 1.74 g of "QUARTAMIN 60W" (tradename; cetyltrimethylammonium chloride; active ingredient: 30% by mass) available from Kao Corporation with 98.26 g of ion-exchanged water. The thus prepared aqueous solution was mixed with an oil phase prepared by mixing 40 g of a model fragrance material A and 10 g of tetraethoxysilane (TEOS), and the resulting mixed solution was emulsified using a homomixer whose rotating speed was set to 8500 rpm. At this time, the average particle size of emulsified droplets in the resulting emulsion was 2.7 μm. After adjusting a pH value of the emulsion to 3.9 using a 1 N sodium hydroxide aqueous solution, the emulsion was transferred into a separable flask equipped with an agitation blade and a condenser, and stirred therein at 160 rpm for 17 h while maintaining the liquid temperature at 30° C.

Step (2)

Next, while maintaining the liquid temperature at 30° C., 5.7 g of TEOS was added dropwise to the resulting suspension having a pH value of 3.2 over 320 min. After completion of the dropwise addition, the suspension was further continuously stirred for 18 h and then cooled, thereby obtaining a suspension containing microcapsules having an average particle size of 4.0 μm in which the model fragrance material A was encapsulated by amorphous silica, as shown in FIG. 1. The encapsulation rates of hexyl acetate, tetrahydrolinalol and hexylcinnamyl aldehyde among the fragrance components contained in the model fragrance material A were 82%, 84% and 100%, respectively.

Figure 2:
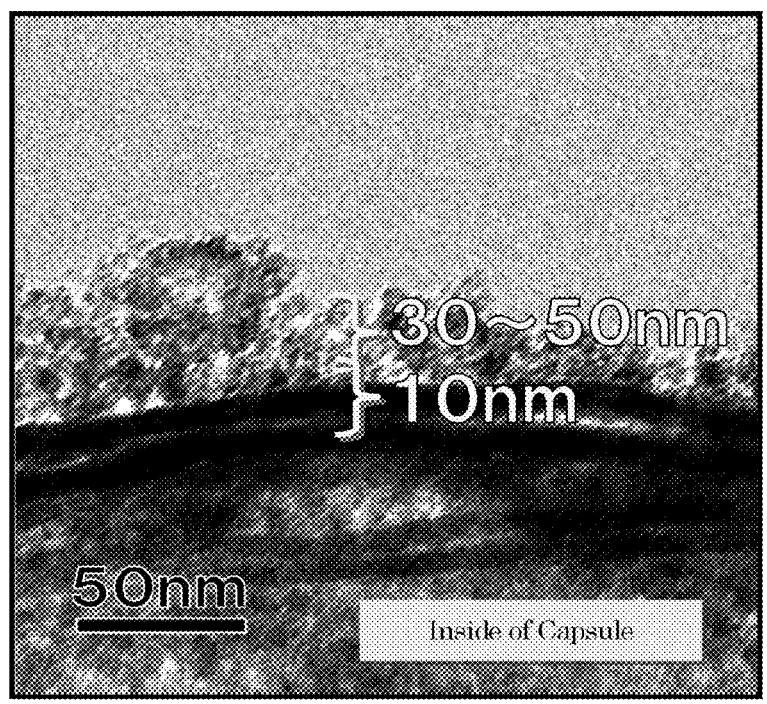
FIG. 2 is a higher-magnification micrograph of transmission electron microscope (TEM) showing microcapsules obtained in Example 1.

In addition, in the resulting microcapsules, as shown in FIG. 2, the first shell had a thickness of about 10 nm, and the second shell had a thickness of not less than 30 nm and not more than 50 nm.

Comparative Example 1 (Production of Microcapsules Including First Shell Only)

Step (1)"

An aqueous solution was prepared by diluting 1.74 g of "QUARTAMIN 60W" (tradename; cetyltrimethylammonium chloride; active ingredient: 30% by mass) available from Kao Corporation with 98.26 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 8500 rpm. At this time, the average particle size of emulsified droplets in the resulting emulsion was 3.4 μm. After adjusting a pH value of the emulsion to 4.2 using a 1 N sodium hydroxide aqueous solution, the emulsion was transferred into a separable flask equipped with an agitation blade and a condenser, and stirred therein at 160 rpm for 23 h while maintaining the liquid temperature at 50° C., thereby obtaining a suspension containing microcapsules having an average particle size of 3.2 μm. The encapsulation rates of hexyl acetate, tetrahydrolinalol and hexylcinnamyl aldehyde among the fragrance components contained in the model fragrance material A were 65%, 71% and 97%, respectively.

Comparative Example 2 (Production of Microcapsules Including First Shell Only)

Step (1)"

An aqueous solution was prepared by diluting 1.86 g of "QUARTAMIN 86W" (tradename; stearyltrimethylammonium chloride; active ingredient: 28% by mass) available from Kao Corporation with 96.52 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 8500 rpm. At this time, the average particle size of emulsified droplets in the resulting emulsion was 3.5 μm. After adjusting a pH value of the emulsion to 4.4 using a 1 N sodium hydroxide aqueous solution, the emulsion was transferred into a separable flask equipped with an agitation blade and a condenser, and stirred therein at 160 rpm for 24 h while maintaining the liquid temperature at 50° C., followed by cooling the resulting emulsion, thereby obtaining a slurry containing microcapsules. However, the microcapsules contained in the slurry were aggregated together, and the average particle size of the thus aggregated microcapsules was 39.6 μm. The encapsulation rates of hexyl acetate, tetrahydrolinalol and hexylcinnamyl aldehyde among the fragrance components contained in the model fragrance material A were 35%, 46% and 77%, respectively. The microcapsules obtained in Comparative Example 2 were not evaluated for storage stability thereof.

Comparative Example 3 (Production of Microcapsules Including First Shell and Second Shell)

Step (1)'

An aqueous solution was prepared by diluting 2.78 g of "QUARTAMIN 60W" (tradename; cetyltrimethylammonium chloride; active ingredient; 30% by mass) available from Kao Corporation with 157.22 g of ion-exchanged water. The thus prepared aqueous solution was mixed with an oil phase prepared by mixing 128 g of a model fragrance material A and 32 g of tetraethoxysilane (TEOS), and the resulting mixed solution was emulsified using a homomixer whose rotating speed was set to 9000 rpm. At this time, the average particle size of emulsified droplets in the resulting emulsion was 2.6 μm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 17 h while maintaining the liquid temperature at 30° C.

Step (2)'

Next, 50 g of the resulting suspension was transferred into an additional flask, and after adjusting a pH value of the suspension to 3.9 using a 0.1 N sodium hydroxide aqueous solution, 3.0 g of TEOS was added dropwise thereinto over 640 min. After completion of the dropwise addition, the suspension was further continuously stirred for 22 h. As a result, the suspension suffered from increase in viscosity with aggregation of the obtained capsules, and further suffered from coagulation, thereby failing to exhibit a flowability.

The results of Example 1 and Comparative Examples 1 to 3 are shown in Tables 5 and 6.

TABLE 5

Microcapsules including first shell and second shell

| | Model fragrance material encapsulated | Surfactant | Method of adding TEOS | Mass ratio of TEOS/ materials encapsulated | pH at initial stage of reaction | Reaction temperature | Average particle size of emulsified particles (μm) | Average particle size of microcapsules at end of reaction (μm) |
|---|---|---|---|---|---|---|---|---|
| Example 1 | A | CTAC | 1) in situ | 1) 25/100 | 1) 3.9 | 1) 30° C. | 2.7 | 4.0 |
| | | | 2) Added dropwise over 320 min | 2) 14/100 | 2) 3.2 | 2) 50° C. | | |
| Comparative Example 1 | A | CTAC | 1) in situ | 1) 25/100 | 1) 4.2 | 1) 50° C. | 3.4 | 3.2 |
| Comparative Example 2 | A | STAC | 1) in situ | 1) 25/100 | 1) 4.4 | 1) 50° C. | 3.5 | 39.6 |

TABLE 5-continued

Microcapsules including first shell and second shell

|  | Model fragrance material encapsulated | Surfactant | Method of adding TEOS | Mass ratio of TEOS/ materials encapsulated | pH at initial stage of reaction | Reaction temperature | Average particle size of emulsified particles (μm) | Average particle size of microcapsules at end of reaction (μm) |
|---|---|---|---|---|---|---|---|---|
| Comparative Example 3 | A | CTAC | 1) in situ<br>2) Added dropwise over 640 min | 1) 25/100<br>2) 15/100 | 1) 3.7<br>2) 3.9 | 1) 30° C.<br>2) 30° C. | 2.6 | No flowability |

Note:
"TEOS" is an abbreviation of tetraethoxysilane;
"1)" and "2)" indicate respective conditions for production of first shell and second shell;
"CTAC" and "STAC" are abbreviations of cetyltrimethylammonium chloride and stearyltrimethylammonium chloride, respectively; and "in situ" means the method of previously mixing TEOS and respective model fragrance materials.

TABLE 6

| Model fragrance material encapsulated | Long-term storage test of fragrance materials in softener (retentivity of fragrance materials) | | |
|---|---|---|---|
| | Hexyl acetate | Tetrahydro-linalol | Hexylcinnamyl aldehyde |
| Example 1 | A | 2 days: 84%<br>24 days: 79% | 2 days: 86%<br>24 days: 84% | 2 days: 85%<br>24 days: 60% |
| Comparative Example 1 | A | 2 days: 0% | 2 days: 0% | 2 days: 0% |

Example 2 (Production of Microcapsules Including First Shell, Second Shell and Third Shell)

Step (1)

An aqueous solution was prepared by diluting 3.48 g of "QUARTAMIN 60W" (tradename; cetyltrimethylammonium chloride; active ingredient; 30% by mass) available from Kao Corporation with 196.52 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 8500 rpm. At this time, the average particle size of emulsified droplets in the resulting emulsion was 2.6 μm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (2)

Next, after raising an inside temperature of the flask to 50° C. by heating, 6.05 g of TEOS was added dropwise to the resulting suspension having a pH value of 3.4 over 320 min. After completion of the dropwise addition, the suspension was further continuously stirred for 18 h and then cooled, thereby obtaining a suspension containing microcapsules having an average particle size of 5.4 μm in which the model fragrance material A was encapsulated. The encapsulation rates of hexyl acetate, tetrahydrolinalol and hexylcinnamyl aldehyde among the fragrance components contained in the model fragrance material A were 94%, 91% and 91%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Example 3 (Production of Microcapsules Including First Shell, Second Shell and Third Shell)

Step (1)

An aqueous solution was prepared by diluting 1.74 g of "QUARTAMIN 60W" (tradename; cetyltrimethylammonium chloride; active ingredient: 30% by mass) available from Kao Corporation with 96.26 g of ion-exchanged water. The thus prepared aqueous solution was mixed with an oil phase prepared by mixing 40 g of a model fragrance material B and 10 g of TEOS, and the resulting mixed solution was emulsified using a homomixer whose rotating speed was set to 8500 rpm. At this time, the average particle size of emulsified droplets in the resulting emulsion was 3.0 μm. After adjusting a pH value of the emulsion to 3.9 using a 1 N hydrochloric acid aqueous solution, the emulsion was transferred into a separable flask equipped with an agitation blade and a condenser, and stirred therein at 160 rpm for 24 h while maintaining the liquid temperature at 30° C.

Step (2)

Next, while maintaining the liquid temperature at 30° C., 6.14 g of TEOS was added dropwise to the resulting suspension having a pH value of 3.5 over 320 min. After completion of the dropwise addition, the suspension was further continuously stirred for 18 h and then cooled, thereby obtaining a suspension containing microcapsules having an average particle size of 4.6 μm in which the model fragrance material B was encapsulated. The encapsulation rates of tetrahydrolinalol, citral and 5-damascone among the fragrance components contained in the model fragrance material B were 82%, 77% and 98%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Example 4 (Production of Microcapsules Including First Shell, Second Shell and Third Shell)

Step (1)

An aqueous solution was prepared by diluting 1.86 g of "QUARTAMIN 86W" (tradename; stearyltrimethylammonium chloride; active ingredient: 28% by mass) available from Kao Corporation with 96.52 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 8500 rpm. At this time, the average particle size of emulsified droplets in the resulting emulsion was 2.7 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (2)

Next, while maintaining the liquid temperature at 30° C., 6.05 g of TEOS was added dropwise to the resulting suspension having a pH value of 3.2 over 320 min. After completion of the dropwise addition, the suspension was further continuously stirred for 18 h and then cooled, thereby obtaining a suspension containing microcapsules having an average particle size of 4.0 µm in which the model fragrance material A was encapsulated. In the resulting suspension, the microcapsules were kept in a dispersed state without being floated or precipitated. The encapsulation rates of hexyl acetate, tetrahydrolinalol and hexylcinnamyl aldehyde among the fragrance components contained in the model fragrance material A were 81%, 89% and 100%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Example 5 (Production of Microcapsules Including First Shell, Second Shell and Third Shell)

Step (1) An aqueous solution was prepared by diluting 1.74 g of "QUARTAMIN 60W" (tradename; cetyltrimethylammonium chloride; active ingredient: 30% by mass) available from Kao Corporation with 96.26 g of ion-exchanged water. The thus prepared aqueous solution was mixed with an oil phase prepared by mixing 40 g of a model fragrance material C (Table 3) and 10 g of TEOS, and the resulting mixed solution was emulsified using a homomixer whose rotating speed was set to 8500 rpm. At this time, the average particle size of emulsified droplets in the resulting emulsion was 2.8 µm. After adjusting a pH value of the emulsion to 3.7 using a 1 N hydrochloric acid aqueous solution, the emulsion was transferred into a separable flask equipped with an agitation blade and a condenser, and stirred therein at 160 rpm for 24 h while maintaining the liquid temperature at 30° C.

Step (2)

Next, while maintaining the liquid temperature at 30° C., 6.14 g of TEOS was added dropwise to the resulting suspension having a pH value of 3.2 over 320 min. After completion of the dropwise addition, the suspension was further continuously stirred for 24 h and then cooled, thereby obtaining a suspension containing microcapsules having an average particle size of 3.9 µm in which the model fragrance material C was encapsulated. The encapsulation rates of 1-menthol, hexyl salicylate and isopropyl myristate among the fragrance components contained in the model fragrance material C were 86%, 97% and 100%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Example 6 (Production of Microcapsules Including First Shell, Second Shell and Third Shell)

Step (1)

An aqueous solution was prepared by diluting 1.74 g of "QUARTAMIN 60W" (tradename; cetyltrimethylammonium chloride; active ingredient; 30% by mass) available from Kao Corporation with 98.26 g of ion-exchanged water. The thus prepared aqueous solution was mixed with an oil phase prepared by mixing 40 g of a model fragrance material A and 6 g of TEOS, and the resulting mixed solution was emulsified using a homomixer whose rotating speed was set to 4500 rpm. At this time, the average particle size of emulsified droplets in the resulting emulsion was 7.5 µm. After adjusting a pH value of the emulsion to 3.9 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (2)

Next, while maintaining the inside temperature of the flask at 30° C., 6.05 g of TEOS was added dropwise to the resulting suspension having a pH value of 3.5 over 320 min. After completion of the dropwise addition, the suspension was further continuously stirred for 18 h and then cooled, thereby obtaining a suspension containing microcapsules having an average particle size of 7.3 µm in which the model fragrance material A was encapsulated. The encapsulation rates of hexyl acetate, tetrahydrolinalol and hexylcinnamyl aldehyde among the fragrance components contained in the model fragrance material A were 58%, 63% and 87%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Comparative Example 4 (Production of Microcapsules Including First Shell and Third Shell Only)

Step (1)"

An aqueous solution was prepared by diluting 1.86 g of "QUARTAMIN 86W" (tradename; stearyltrimethylammonium chloride; active ingredient: 28% by mass) available from Kao Corporation with 96.52 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 8500 rpm. At this time, the average particle size of emulsified droplets in the resulting emulsion was 2.7 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 24 h while maintaining the liquid temperature at 30° C., thereby obtaining a suspension containing microcapsules having an average particle size of 2.8 µm. The encapsulation rates of hexyl acetate, tetrahydrolinalol and hexylcinnamyl aldehyde among the fragrance components contained in the model fragrance material A were 84%, 88% and 100%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Comparative Example 5 (Production of Microcapsules Including First Shell and Third Shell Only)

Step (1)"

An aqueous solution was prepared by diluting 5.0 g of "QUARTAMIN 60W" (tradename; cetyltrimethylammonium chloride; active ingredient: 30% by mass) available from Kao Corporation with 145 g of ion-exchanged water. The thus prepared aqueous solution was mixed with an oil phase prepared by mixing 16.5 g of a model fragrance material A and 16.5 g of TEOS, and the resulting mixed solution was emulsified using a homomixer whose rotating speed was set to 8500 rpm. At this time, the average particle size of emulsified droplets in the resulting emulsion was 2.5 μm.

On the other hand, 150 g of water whose pH value had been adjusted to 11.5 using a 0.1 N sodium hydroxide aqueous solution was prepared, and added dropwise to the above-prepared emulsion containing the model fragrance material A and TEOS. The resulting mixture was stirred at room temperature for 96 h to obtain a slurry. As a result, it was confirmed that microcapsules contained in the slurry were aggregated, and had an average particle size of 11.3 μm. The encapsulation rates of hexyl acetate, tetrahydrolinalol and hexylcinnamyl aldehyde among the fragrance components contained in the model fragrance material A were 0%, 36% and 0%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Comparative Example 6 (Production of Microcapsules Including First Shell and Third Shell Only)

Step (1)"

An aqueous solution was prepared by diluting 2.68 g of "QUARTAMIN 60W" (tradename; cetyltrimethylammonium chloride; active ingredient: 30% by mass) available from Kao Corporation with 80.5 g of ion-exchanged water. The thus prepared aqueous solution was mixed with an oil phase prepared by mixing 138 g of a model fragrance material A and 12 g of TEOS, and the resulting mixed solution was emulsified using a homomixer whose rotating speed was set to 9000 rpm. At this time, the average particle size of emulsified droplets in the resulting emulsion was 2.5 μm.

On the other hand, 115.25 g of water whose pH value had been adjusted to 3.8 using 0.1 N hydrochloric acid was prepared, and added dropwise to the above-prepared emulsion containing the model fragrance material A and TEOS. The resulting mixture was stirred at room temperature for 96 h to obtain a slurry. As a result, it was confirmed that microcapsules contained in the slurry had an average particle size of 2.9 μm. The encapsulation rates of hexyl acetate, tetrahydrolinalol and hexylcinnamyl aldehyde among the fragrance components contained in the model fragrance material A were 21%, 18% and 99%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Comparative Example 7 (Production of Microcapsules Including First Shell and Third Shell Only)

Step (1)"

An aqueous solution was prepared by diluting 1.25 g of "QUARTAMIN 60W" (tradename; cetyltrimethylammonium chloride; active ingredient: 30% by mass) available from Kao Corporation with 73.4 g of ion-exchanged water. The thus prepared aqueous solution was mixed with 75 g of a model fragrance material A, and the resulting mixed solution was emulsified using a homomixer whose rotating speed was set to 8500 rpm. At this time, the average particle size of emulsified droplets in the resulting emulsion was 2.6 μm.

After adding dropwise 11.8 g of TEOS to the above obtained emulsion over 30 min, the resulting mixture was reacted at room temperature for 17 h while maintaining a pH value thereof at 3.9 using a 0.1 N sodium hydroxide aqueous solution. As a result, it was confirmed that microcapsules contained in the resulting slurry were aggregated, and had an average particle size of 50.5 μm. The encapsulation rates of hexyl acetate, tetrahydrolinalol and hexylcinnamyl aldehyde among the fragrance components contained in the model fragrance material A were 39%, 38% and 92%, respectively.

Step (3)

Next, 2 g of the resulting suspension containing the microcapsules was dispersed in 0.5 g of an aqueous solution containing 3% of an isobutylene-maleic acid alternating copolymer "DEMOL EP" (tradename; active ingredient: 25%) available from Kao Corporation, thereby obtaining a suspension containing microcapsules.

Comparative Example 8 (Production of Microcapsules Including First Shell)

Step (1)

An aqueous solution was prepared by diluting 1.7 g of "QUARTAMIN 60W" (tradename; cetyltrimethylammonium chloride; active ingredient: 30% by mass) available from Kao Corporation with 98.3 g of ion-exchanged water. The thus prepared aqueous solution was mixed with an oil phase prepared by mixing 25 g of a model fragrance material A and 25 g of TEOS, and the resulting mixed solution was emulsified using a homomixer whose rotating speed was set to 8500 rpm. At this time, the average particle size of emulsified droplets in the resulting emulsion was 2.5 μm. After adjusting a pH value of the emulsion to 3.5 using 1 N hydrochloric acid, the emulsion was transferred into a separable flask equipped with an agitation blade and a condenser, and stirred therein at 160 rpm for 48 h while maintaining the liquid temperature at 30° C. However, the resulting slurry exhibited no flowability and was solidified. The encapsulation rates of hexyl acetate, tetrahydrolinalol and hexylcinnamyl aldehyde among the fragrance components contained in the model fragrance material A were 43%, 48% and 100%, respectively.

Example 7 (Production of Microcapsules Including First Shell and Second Shell)

Step (1)

An aqueous solution was prepared by diluting 2.78 g of "QUARTAMIN 60W" (tradename; cetyltrimethylammonium chloride; active ingredient; 30% by mass) available from Kao Corporation with 157.22 g of ion-exchanged water. The thus prepared aqueous solution was mixed with an oil phase prepared by mixing 128 g of a model fragrance material A and 32 g of tetraethoxysilane (TEOS), and the resulting mixed solution was emulsified using a homomixer whose rotating speed was set to 9000 rpm. At this time, the average particle size of emulsified droplets in the resulting emulsion was 2.6 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 17 h while maintaining the liquid temperature at 30° C.

Step (2)

Next, 50 g of the resulting suspension was transferred into an additional flask, and after adjusting a pH value of the suspension to 2.2 using a 1 N hydrochloric acid aqueous solution, 2.9 g of TEOS was added dropwise thereinto over 640 min After completion of the dropwise addition, the suspension was further continuously stirred for 22 h and then cooled, thereby obtaining a suspension containing microcapsules having an average particle size of 2.2 µm in which the model fragrance material A was encapsulated by amorphous silica. The encapsulation rates of hexyl acetate, tetrahydrolinalol and hexylcinnamyl aldehyde among the fragrance components contained in the model fragrance material A were 68%, 77% and 92%, respectively.

Step (3)

Next, 2 g of the resulting suspension containing the microcapsules was dispersed in 0.5 g of an aqueous solution containing 3% of gum arabic.

Example 8 (Production of Microcapsules Including First Shell and Second Shell)

Step (1)

An aqueous solution was prepared by diluting 3.48 g of "QUARTAMIN 60W" (tradename; cetyltrimethylammonium chloride; active ingredient; 30% by mass) available from Kao Corporation with 196.52 g of ion-exchanged water. The thus prepared aqueous solution was mixed with an oil phase prepared by mixing 80 g of a model fragrance material A and 20 g of tetraethoxysilane (TEOS), and the resulting mixed solution was emulsified using a homomixer whose rotating speed was set to 9000 rpm. At this time, the average particle size of emulsified droplets in the resulting emulsion was 2.2 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 18 h while maintaining the liquid temperature at 30° C.

Step (2)

Next, 130 g of the resulting suspension was transferred into an additional vessel, and while maintaining the liquid temperature at 30° C., 5.1 g of TEOS was added dropwise into the suspension having a pH value of 2.9 over 100 min. After completion of the dropwise addition, the suspension was further continuously stirred for 20 h and then cooled, thereby obtaining a suspension containing microcapsules having an average particle size of 2.3 µm in which the model fragrance material A was encapsulated. The encapsulation rates of hexyl acetate, tetrahydrolinalol and hexylcinnamyl aldehyde among the fragrance components contained in the model fragrance material A were 98%, 100% and 100%, respectively.

Step (3)

Next, 2 g of the resulting suspension containing the microcapsules was dispersed in 0.5 g of an aqueous solution containing 3% of gum arabic.

Example 9 (Production of Microcapsules Including First Shell and Second Shell)

Step (1)

An aqueous solution was prepared by diluting 3.48 g of "QUARTAMIN 60W" (tradename; cetyltrimethylammonium chloride; active ingredient; 30% by mass) available from Kao Corporation with 196.52 g of ion-exchanged water. The thus prepared aqueous solution was mixed with an oil phase prepared by mixing 80 g of a model fragrance material A and 20 g of tetraethoxysilane (TEOS), and the resulting mixed solution was emulsified using a homomixer whose rotating speed was set to 9000 rpm. At this time, the average particle size of emulsified droplets in the resulting emulsion was 2.2 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 18 h while maintaining the liquid temperature at 30° C.

Step (2)

Next, 130 g of the resulting suspension was transferred into an additional vessel, and while maintaining the liquid temperature at 30° C., 5.1 g of TEOS was added dropwise into the suspension having a pH value of 2.9 over 500 min. After completion of the dropwise addition, the suspension was further continuously stirred for 20 h and then cooled, thereby obtaining a suspension containing microcapsules having an average particle size of 2.3 µm in which the model fragrance material A was encapsulated. The encapsulation rates of hexyl acetate, tetrahydrolinalol and hexylcinnamyl aldehyde among the fragrance components contained in the model fragrance material A were 88%, 91% and 98%, respectively.

Step (3)

Next, 2 g of the resulting suspension containing the microcapsules was dispersed in 0.5 g of an aqueous solution containing 3% of gum arabic.

Example 10 (Production of Microcapsules Including First Shell and Second Shell)

Step (1)

An aqueous solution was prepared by diluting 1.74 g of "QUARTAMIN 60W" (tradename; cetyltrimethylammonium chloride; active ingredient: 30% by mass) available from Kao Corporation with 98.26 g of ion-exchanged water. The thus prepared aqueous solution was mixed with an oil phase prepared by mixing 40 g of a model fragrance material A and 14 g of tetraethoxysilane (TEOS), and the resulting mixed solution was emulsified using a homomixer whose rotating speed was set to 9000 rpm. At this time, the average particle size of emulsified droplets in the resulting emulsion was 2.2 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 17 h while maintaining the liquid temperature at 30° C.

Step (2)

Next, while maintaining the liquid temperature at 30° C., 5.8 g of TEOS was added dropwise into the suspension having a pH value of 3.2 over 500 min. After completion of the dropwise addition, the suspension was further continuously stirred for 18 h and then cooled, thereby obtaining a suspension containing microcapsules having an average particle size of 2.3 µm in which were the model fragrance material A was encapsulated, as shown in FIG. 1. The encapsulation rates of hexyl acetate, tetrahydrolinalol and hexylcinnamyl aldehyde among the fragrance components contained in the model fragrance material A were 76%, 85% and 91%, respectively.

Step (3)

Next, 2 g of the resulting suspension containing the microcapsules was dispersed in 0.5 g of an aqueous solution containing 3% of gum arabic.

Example 11 (Production of Microcapsules Including First Shell, Cationized Second Shell and Third Shell)

Step (1)

An aqueous solution was prepared by diluting 1.74 g of "QUARTAMIN 60W" (tradename; cetyltrimethylammonium chloride; active ingredient: 30% by mass) available from Kao Corporation with 98.26 g of ion-exchanged water. The thus prepared aqueous solution was mixed with an oil phase prepared by mixing 40 g of a model fragrance material A and 10 g of TEOS, and the resulting mixed solution was emulsified using a homomixer whose rotating speed was set to 9000 rpm. At this time, the average particle size of emulsified droplets in the resulting emulsion was 2.2 µm. After adjusting a pH value of the emulsion to 3.7 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (1-1)

Then, 0.86 g of "MERQUAT 100" (cationic group equivalent: 6.2 meq/g; active ingredient: 42% by mass) available from The Lubrisol Corporation, was diluted with ion-exchanged water to adjust a total amount thereof to 12 g, thereby obtaining a cationic polymer aqueous solution containing 3% by mass of the active ingredient. The thus obtained aqueous solution was added to the suspension obtained in the step (1) while maintaining the liquid temperature at 30° C.

Step (2)

Next, while maintaining the liquid temperature at 30° C., 6.2 g of TEOS was added dropwise into the suspension having a pH value of 3.1 over 320 min. After completion of the dropwise addition, the suspension was further continuously stirred for 18 h and then cooled, thereby obtaining a suspension containing microcapsules having an average particle size of 3.1 µm in which the model fragrance material A was encapsulated. In the resulting suspension, the microcapsules were kept in a dispersed state without being floated or precipitated. The encapsulation rates of hexyl acetate, tetrahydrolinalol and hexylcinnamyl aldehyde among the fragrance components contained in the model fragrance material A were 98%, 92% and 100%, respectively.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

The results of Examples 2 to 11 and Comparative Examples 4 to 8 are shown in Tables 7 and 8.

TABLE 7

Microcapsules including first shell and second shell

| | Model fragrance material encapsulated | Surfactant | Method of adding TEOS | Mass ratio of TEOS/ materials encapsulated | pH at initial stage of reaction | Reaction temp. | Average particle size of emulsified particles (µm) | Average particle size of microcapsules at end of reaction (µm) | Third shell Organic polymer compound |
|---|---|---|---|---|---|---|---|---|---|
| Example 2 | A | CTAC | 1) in situ<br>2) Added dropwise over 320 min | 1) 25/100<br>2) 15/100 | 1) 3.7<br>2) 3.4 | 1) 30° C.<br>2) 50° C. | 2.6 | 5.4 | "DEMOL EP" |
| Example 3 | B | CTAC | 1) in situ<br>2) Added dropwise over 320 min | 1) 25/100<br>2) 15/100 | 1) 3.9<br>2) 3.5 | 1) 30° C.<br>2) 30° C. | 3.0 | 4.6 | "DEMOL EP" |
| Example 4 | A | STAC | 1) in situ<br>2) Added dropwise over 320 min | 1) 25/100<br>2) 15/100 | 1) 3.7<br>2) 3.2 | 1) 30° C.<br>2) 30° C. | 2.7 | 4.0 | "DEMOL EP" |
| Example 5 | C | CTAC | 1) in situ<br>2) Added dropwise over 320 min | 1) 25/100<br>2) 15/100 | 1) 3.7<br>2) 3.2 | 1) 30° C.<br>2) 30° C. | 2.8 | 3.9 | "DEMOL EP" |
| Example 6 | A | CTAC | 1) in situ<br>2) Added dropwise over 320 min | 1) 15/100<br>2) 15/100 | 1) 3.9<br>2) 3.5 | 1) 30° C.<br>2) 30° C. | 7.5 | 7.3 | "DEMOL EP" |
| Example 7 | A | CTAC | 1) in situ<br>2) Added dropwise over 640 min | 1) 25/100<br>2) 15/100 | 1) 3.7<br>2) 2.2 | 1) 30° C.<br>2) 30° C. | 2.6 | 2.2 | Gum arabic |
| Example 8 | A | CTAC | 1) in situ<br>2) Added dropwise over 100 min | 1) 25/100<br>2) 15/100 | 1) 3.7<br>2) 2.9 | 1) 30° C.<br>2) 30° C. | 2.2 | 2.3 | Gum arabic |

TABLE 7-continued

Microcapsules including first shell and second shell

| | Model fragrance material encapsulated | Surfactant | Method of adding TEOS | Mass ratio of TEOS/ materials encapsulated | pH at initial stage of reaction | Reaction temp. | Average particle size of emulsified particles (μm) | Average particle size of microcapsules at end of reaction (μm) | Third shell Organic polymer compound |
|---|---|---|---|---|---|---|---|---|---|
| Example 9 | A | CTAC | 1) in situ<br>2) Added dropwise over 500 min | 1) 25/100<br>2) 15/100 | 1) 3.7<br>2) 2.9 | 1) 30° C.<br>2) 30° C. | 2.2 | 2.3 | Gum arabic |
| Example 10 | A | CTAC | 1) in situ<br>2) Added dropwise over 500 min | 1) 35/100<br>2) 15/100 | 1) 3.7<br>2) 3.2 | 1) 30° C.<br>2) 30° C. | 2.2 | 2.3 | Gum arabic |
| Example 11 | A | CTAC | 1) in situ<br>2) Added dropwise over 320 min | 1) 25/100<br>2) 15/100 | 1) 3.7<br>2) 3.1 | 1) 30° C.<br>2) 30° C. | 2.2 | 3.1 | Gum arabic |
| Comparative Example 4 | A | STAC | 1) in situ | 1) 25/100 | 1) 3.7 | 1) 30° C. | 2.7 | 2.8 | "DEMOL EP" |
| Comparative Example 5 | A | CTAC | 1) in situ | 1) 100/100 | 1) 11.5 | 1) 30° C. | 2.5 | 11.3 | "DEMOL EP" |
| Comparative Example 6 | A | CTAC | 1) in situ | 1) 9/100 | 1) 3.8 | 1) 30° C. | 2.5 | 2.9 | "DEMOL EP" |
| Comparative Example 7 | A | CTAC | 1) Added dropwise over 30 min | 1) 16/100 | 1) 3.9 | 1) 30°C | 2.6 | 50.5 | "DEMOL EP" |
| Comparative Example 8 | A | CTAC | 1) in situ | 1) 100/100 | 1) 3.5 | 1) 30° C. | 2.5 | No flowability | |

Note:
"TEOS" is an abbreviation of tetraethoxysilane;
"1)" and "2)" indicate respective conditions for production of first shell and second shell;
"CTAC" and "STAC" are abbreviations of cetyltrimethylammonium chloride and stearyltrimethylammonium chloride, respectively;
"in situ" means the method of previously mixing TEOS and respective model fragrance materials; and In Example 11, the microcapsules obtained after forming the first shell were treated with a cationic polymer (polydiallyldimethylammonium chloride "MERQUAT 100"; treated concentration: 3.0% by mass) before forming the second shell thereon.

TABLE 8

| | Model fragrance material encapsulated | Long-term storage test of fragrance materials in liquid detergent (retentivity of fragrance materials) | | | |
|---|---|---|---|---|---|
| | | Hexyl acetate | Tetrahydrolinalol | Hexylcinnamyl aldehyde | Citral |
| Example 2 | A | 2 days: 62%;<br>2 weeks: 54% | 2 days: 64%;<br>2 weeks: 50% | 2 days: 67%;<br>2 weeks: 55% | — |
| Example 3 | B | — | 2 days: 99%;<br>1 week: 72%;<br>2 weeks: 57% | — | 2 days: 63%;<br>1 week: 31%;<br>2 weeks: 12% |
| Example 4 | A | 2 days: 62%;<br>3 weeks: 57% | 2 days: 63%;<br>3 weeks: 60% | 2 days: 62%;<br>3 weeks: 51% | |
| Example 5 | C | — | — | — | — |
| Example 6 | A | 2 days: 83%;<br>2 weeks: 39% | 2 days: 84%;<br>2 weeks: 40% | 2 days: 66%;<br>2 weeks: 33% | — |
| Example 7 | A | 2 days: 70%;<br>3 weeks: 60% | 2 days: 55%;<br>3 weeks: 50% | 2 days: 58%;<br>3 weeks: 54% | — |
| Example 8 | A | 2 days: 51%;<br>3 weeks: 24% | 2 days: 52%;<br>3 weeks: 28% | 2 days: 59%;<br>3 weeks: 28% | — |
| Example 9 | A | 2 days: 88%;<br>3 weeks: 38% | 2 days: 94%;<br>3 weeks: 42% | 2 days: 71%;<br>3 weeks: 34% | — |
| Example 10 | A | 2 days: 71%;<br>3 weeks: 49% | 2 days: 70%;<br>3 weeks: 49% | 2 days: 68%;<br>3 weeks: 40% | — |
| Example 11 | A | 2 days: 71%;<br>2 weeks: 65% | 2 days: 69%;<br>3 weeks: 60% | 2 days: 76%;<br>3 weeks: 51% | — |
| Comparative Example 4 | A | 2 days: 0% | 2 days: 0% | 2 days: 0% | — |
| Comparative Example 5 | A | 2 days: 0% | 2 days: 0% | 2 days: 0% | — |
| Comparative Example 6 | A | 2 days: 0% | 2 days: 0% | 2 days: 0% | — |
| Comparative Example 7 | A | 2 days: 30%;<br>2 weeks: 0% | 2 days: 34%;<br>2 weeks: 23% | 2 days: 40%;<br>2 weeks: 27% | — |

TABLE 8-continued

| | Long-term storage test of fragrance materials in liquid detergent (retentivity of fragrance materials) | | | |
|---|---|---|---|---|
| | δ-Damascone | l-Menthol | Hexyl salicylate | Isopropyl myristate |
| Example 2 | — | — | — | — |
| Example 3 | 2 days: 90%; 1 week: 76%; 2 weeks: 60% | — | — | — |
| Example 4 | — | — | — | — |
| Example 5 | — | 2 days: 51%; 1 week: 50%; 3 weeks: 47% | 2 days: 55%; 1 week: 49%; 3 weeks: 46% | 2 days: 60%; 1 week: 52%; 3 weeks: 47% |
| Example 6 | — | — | — | — |
| Example 7 | — | — | — | — |
| Example 8 | — | — | — | — |
| Example 9 | — | — | — | — |
| Example 10 | — | — | — | — |
| Example 11 | — | — | — | — |
| Comparative Example 4 | — | — | — | — |
| Comparative Example 5 | — | — | — | — |
| Comparative Example 6 | — | — | — | — |
| Comparative Example 7 | — | — | — | — |

Example 12 (Production of Microcapsules Including First Shell, Second Shell and Third Shell)

Step (1)

An aqueous solution was prepared by diluting 3.48 g of "QUARTAMIN 60W" (tradename; cetyltrimethylammonium chloride; active ingredient; 30% by mass) available from Kao Corporation with 196.52 g of ion-exchanged water. The thus prepared aqueous solution was mixed with an oil phase prepared by mixing 80 g of a model fragrance material D and 20 g of TEOS, and the resulting mixed solution was emulsified using a homomixer whose rotating speed was set to 9000 rpm. At this time, the average particle size of emulsified droplets in the resulting emulsion was 2.1 After adjusting a pH value of the emulsion to 3.8 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (2)

Next, while maintaining the liquid temperature at 30° C., 2.0 g of TEOS was added dropwise into the suspension having a pH value of 3.1 over 320 min. After completion of the dropwise addition, the suspension was further continuously stirred for 18 h and then cooled, thereby obtaining a suspension containing microcapsules having an average particle size of 2.2 μm in which the model fragrance material D was encapsulated. In the resulting suspension, the microcapsules were kept in a dispersed state without being floated or precipitated. The encapsulation rate of the silicic acid ester represented by the formula (1) among the fragrance components contained in the model fragrance material D was 65%.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

Example 13 (Production of Microcapsules Including First Shell, Cationized Second Shell and Third Shell)

Step (1)

An aqueous solution was prepared by diluting 3.48 g of "QUARTAMIN 60W" (tradename; cetyltrimethylammonium chloride; active ingredient: 30% by mass) available from Kao Corporation with 196.52 g of ion-exchanged water. The thus prepared aqueous solution was mixed with an oil phase prepared by mixing 80 g of a model fragrance material D and 20 g of TEOS, and the resulting mixed solution was emulsified using a homomixer whose rotating speed was set to 9000 rpm. At this time, the average particle size of emulsified droplets in the resulting emulsion was 2.1 μm. After adjusting a pH value of the emulsion to 3.9 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (1-1)

Then, 0.46 g of "MERQUAT 100" (cationic group equivalent: 6.2 meq/g; active ingredient: 42% by mass) available from The Lubrisol Corporation was diluted with ion-exchanged water to adjust a total amount thereof to 6.4 g, thereby obtaining a cationic polymer aqueous solution containing 3% by mass of the active ingredient. The thus obtained aqueous solution was added to 80 g of the suspension obtained in the step (1) while maintaining the liquid temperature at 30° C.

Step (2)

Next, while maintaining the liquid temperature at 30° C., 5.0 g of TEOS was added dropwise into the suspension having a pH value of 3.2 over 320 min. After completion of the dropwise addition, the suspension was further continuously stirred for 18 h and then cooled, thereby obtaining a suspension containing microcapsules having an average particle size of 2.2 μm in which the model fragrance material D was encapsulated. In the resulting suspension, the microcapsules were kept in a dispersed state without being floated or precipitated. The encapsulation rate of the silicic acid ester represented by the formula (1) among the fragrance components contained in the model fragrance material D was 95%.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

Example 14 (Production of Microcapsules Including First Shell, Cationized Second Shell and Third Shell)

Step (1)

An aqueous solution was prepared by diluting 3.48 g of "QUARTAMIN 60W" (tradename; cetyltrimethylammonium chloride; active ingredient: 30% by mass) available from Kao Corporation with 196.52 g of ion-exchanged water. The thus prepared aqueous solution was mixed with an oil phase prepared by mixing 80 g of a model fragrance material D and 20 g of TEOS, and the resulting mixed solution was emulsified using a homomixer whose rotating speed was set to 9000 rpm. At this time, the average particle size of emulsified droplets in the resulting emulsion was 2.2 μm. After adjusting a pH value of the emulsion to 3.9 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (1-1)

Then, 0.23 g of "MERQUAT 100" (cationic group equivalent: 6.2 meq/g: active ingredient: 42% by mass) available from The Lubrisol Corporation was diluted with ion-exchanged water to adjust a total amount thereof to 3.2 g, thereby obtaining a cationic polymer aqueous solution containing 3% by mass of the active ingredient. The thus obtained aqueous solution was added to 80 g of the suspension obtained in the step (1) while maintaining the liquid temperature at 30° C.

Step (2)

Next, while maintaining the liquid temperature at 30° C., 3.3 g of TEOS was added dropwise into the suspension having a pH value of 3.6 over 320 min. After completion of the dropwise addition, the suspension was further continuously stirred for 18 h and then cooled, thereby obtaining a suspension containing microcapsules having an average particle size of 2.5 μm in which the model fragrance material D was encapsulated. In the resulting suspension, the microcapsules were kept in a dispersed state without being floated or precipitated. The encapsulation rate of the silicic acid ester represented by the formula (1) among the fragrance components contained in the model fragrance material D was 85%.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

Example 15 (Production of Microcapsules Including First Shell, Cationized Second Shell and Third Shell)

Step (1)

An aqueous solution was prepared by diluting 3.48 g of "QUARTAMIN 60W" (tradename; cetyltrimethylammonium chloride; active ingredient: 30% by mass) available from Kao Corporation with 196.52 g of ion-exchanged water. The thus prepared aqueous solution was mixed with an oil phase prepared by mixing 80 g of a model fragrance material D and 20 g of TEOS, and the resulting mixed solution was emulsified using a homomixer whose rotating speed was set to 9000 rpm. At this time, the average particle size of emulsified droplets in the resulting emulsion was 2.1 μm. After adjusting a pH value of the emulsion to 3.8 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (1-1)

Then, 0.51 g of "MERQUAT 295" (cationic group equivalent: 6.0 meq/g; anionic group equivalent: 0.3 meq/g; active ingredient: 38% by mass) available from The Lubrisol Corporation was diluted with ion-exchanged water to adjust a total amount thereof to 6.4 g, thereby obtaining an aqueous solution containing 3% by mass of the active ingredient. The thus obtained cationic polymer aqueous solution was added to 80 g of the suspension obtained in the step (1) while maintaining the liquid temperature at 30° C.

Step (2)

Next, while maintaining the liquid temperature at 30° C., 3.3 g of TEOS was added dropwise into the suspension having a pH value of 3.2 over 320 min. After completion of the dropwise addition, the suspension was further continuously stirred for 18 h and then cooled, thereby obtaining a suspension containing microcapsules having an average particle size of 2.7 μm in which the model fragrance material D was encapsulated. In the resulting suspension, the microcapsules were kept in a dispersed state without being floated or precipitated. The encapsulation rate of the silicic acid ester represented by the formula (1) among the fragrance components contained in the model fragrance material D was 98%.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

Example 16 (Production of Microcapsules Including First Shell, Cationized Second Shell and Third Shell)

Step (1)

An aqueous solution was prepared by diluting 3.48 g of "QUARTAMIN 60W" (tradename; cetyltrimethylammonium chloride; active ingredient: 30% by mass) available from Kao Corporation with 196.52 g of ion-exchanged water. The thus prepared aqueous solution was mixed with an oil phase prepared by mixing 80 g of a model fragrance material D and 20 g of TEOS, and the resulting mixed solution was emulsified using a homomixer whose rotating speed was set to 9000 rpm. At this time, the average particle size of emulsified droplets in the resulting emulsion was 2.2 µm. After adjusting a pH value of the emulsion to 3.8 using a 1 N sodium hydroxide aqueous solution, the emulsion was transferred into a separable flask equipped with an agitation blade and a condenser, and stirred therein at 160 rpm for 24 h while maintaining the liquid temperature at 30° C.

Step (1-1)

Then, 1.92 g of "MERQUAT 3330PR" (cationic group equivalent: 3.0 meq/g; anionic group equivalent: 3.1 meq/g; active ingredient: 10% by mass) available from The Lubrisol Corporation was diluted with ion-exchanged water to adjust a total amount thereof to 6.4 g, thereby obtaining a cationic polymer aqueous solution containing 3% by mass of the active ingredient. The thus obtained aqueous solution was added to 80 g of the suspension obtained in the step (1) while maintaining the liquid temperature at 30° C.

Step (2)

Next, while maintaining the liquid temperature at 30° C., 3.2 g of TEOS was added dropwise into the suspension having a pH value of 3.2 over 320 min. After completion of the dropwise addition, the suspension was further continuously stirred for 18 h and then cooled, thereby obtaining capsules encapsulating the model fragrance material D. As a result, it was confirmed that the capsules were partially aggregated in the resulting suspension, and the average particle size of the capsules contained the suspension was 104 µm. The encapsulation rate of the silicic acid ester represented by the formula (1) among the fragrance components contained in the model fragrance material D was 89%.

Step (3)

Next, 2 g of the resulting suspension containing the microcapsules was dispersed in 0.5 g of an aqueous solution containing 3% of gum arabic available from Kishida Chemical Co., Ltd., thereby obtaining a suspension containing microcapsules.

The evaluation results of Examples 12 to 16 and Comparative Example 9 are shown in Tables 9 and 10.

TABLE 9

| | Microcapsules including first shell and second shell | | | | |
|---|---|---|---|---|---|
| | Model fragrance material encapsulated | Surfactant | Method of adding TEOS | Kind of cationic polymer compound | Concentration of aqueous solution of cationic polymer compound |
| Example 11 | A | CTAC | 1) in situ 2) Added dropwise over 320 min | Polydiallyldimethylammonium chloride "MERQUAT 100" | 3.0% |
| Example 12 | D | CTAC | 1) in situ 2) Added dropwise over 320 min | — | — |
| Example 13 | D | CTAC | 1) in situ 2) Added dropwise over 320 min | Polydiallyldimethylammonium chloride "MERQUAT 100" | 3.0% |
| Example 14 | D | CTAC | 1) in situ 2) Added dropwise over 320 min | Polydiallyldimethylammonium chloride "MERQUAT 100" | 3.0% |
| Example 15 | D | CTAC | 1) in situ 2) Added dropwise over 320 min | Acrylic acid-diallyldimethylammonium chloride copolymer "MERQUAT 295" | 3.0% |
| Example 16 | D | CTAC | 1) in situ 2) Added dropwise over 320 min | Acrylamide-acrylic acid-diallyldimethylammonium chloride copolymer "MERQUAT 3330PLUS" | 3.0% |

| | Microcapsules including first shell and second shell | | | | | |
|---|---|---|---|---|---|---|
| | Mass ratio of TEOS/materials encapsulated | pH at initial stage of reaction | Reaction temperature | Average particle size of emulsified particles (µm) | Average particle size of microcapsules at end of reaction (µm) | Third shell Organic polymer compound |
| Example 11 | 1) 25/100 2) 15/100 | 1) 3.7 2) 3.1 | 1) 30° C. 2) 30° C. | 2.2 | 3.1 | Gum arabic |
| Example 12 | 1) 25/100 2) 15/100 | 1) 3.8 2) 3.1 | 1) 30° C. 2) 30° C. | 2.1 | 2.2 | Gum arabic |
| Example 13 | 1) 25/100 2) 15/100 | 1) 3.9 2) 3.2 | 1) 30° C. 2) 30° C. | 2.1 | 2.2 | Gum arabic |
| Example 14 | 1) 25/100 2) 15/100 | 1) 3.9 2) 3.6 | 1) 30° C. 2) 30° C. | 2.2 | 2.5 | Gum arabic |

TABLE 9-continued

| | | Microcapsules including first shell and second shell | | | | |
|---|---|---|---|---|---|---|
| Example 15 | 1) 25/100 | 1) 3.8 | 1) 30° C. | 2.1 | 2.7 | Gum arabic |
| | 2) 15/100 | 2) 3.2 | 2) 30° C. | | | |
| Example 16 | 1) 25/100 | 1) 3.8 | 1) 30° C. | 2.2 | 104.0 | Gum arabic |
| | 2) 15/100 | 2) 3.2 | 2) 30° C. | | | |

Note:
"TEOS" is an abbreviation of tetraethoxysilane;
"1)" and "2)" indicate respective conditions for production of first shell and second shell;
"CTAC" and "STAC" are abbreviations of cetyltrimethylammonium chloride and stearyltrimethylammonium chloride, respectively; and "in situ" means the method of previously mixing TEOS and respective model fragrance materials.

TABLE 10

| | Model fragrance material encapsulated | Long-term storage test of silicic acid ester in hair shampoo | |
|---|---|---|---|
| | | Retentivity of tetra-substituted silicic acid ester | Encapsulation rate of silicic acid ester at initial stage of blending |
| Example 12 | D | 3 days: 26%<br>2 weeks: 21% | 50% |
| Example 13 | D | 3 days: 52%<br>2 weeks: 36% | 63% |
| Example 14 | D | 3 days: 49%<br>2 weeks: 37% | 54% |
| Example 15 | D | 3 days: 50%<br>2 weeks: 24% | 60% |
| Example 16 | D | 3 days: 62%<br>2 weeks: 40% | 43% |
| Comparative Example 9 (directly perfumed with silicic acid ester composition) | 1) | 3 days: 0% | — |

Note
1) Geraniol-substituted silicic acid ester composition produced in Production Example 1

As apparently shown in Tables, it was confirmed that the microcapsules according to the present invention are capable of retaining an organic compound as an active ingredient such as fragrance materials therein over a long period of time. In addition, it was confirmed that the microcapsules further containing the third shell including an organic polymer compound are capable of retaining an organic compound as an active ingredient such as fragrance materials therein over a long period of time without occurrence of aggregated capsules even in the presence of a surfactant such as liquid detergents or hair shampoos. As described above, the microcapsules according to the present invention can be suitably used for various products in which active ingredients such as fragrance materials are blended.

The invention claimed is:

1. A process for producing microcapsules, each microcapsule comprising a first shell and a second shell, where each shell comprises silica, and a core comprising at least one organic compound which is encapsulated within the first shell, said process comprising (1) and (2):
   (1) emulsifying an organic phase comprising the at least one organic compound and a tetraalkoxysilane such that a content of the tetraalkoxysilane in the organic phase is not less than 10% by mass and not more than 60% by mass on the basis of the organic compound, in a water phase comprising a surfactant, and subjecting the resulting emulsion to a sol-gel reaction under acidic conditions to form microcapsules each comprising the core and the first shell; and
   (2) further adding a tetraalkoxysilane to a water dispersion comprising the microcapsules obtained in the step said (1) emulsifying, and subjecting the obtained mixture to a sol-gel reaction while maintaining an initial pH value in the sol-gel reaction of the step said (2) further adding below an initial pH value in the sol-gel reaction of the step said (1) emulsifying, thereby forming to form the microcapsules, each of which comprising the second shell encapsulating the first shell.

2. The process for producing microcapsules according to claim 1, further comprising the following step (3):
   (3) mixing a dispersion comprising the microcapsules obtained in said (2) further adding with an aqueous solution of an organic polymeric compound to form microcapsules comprising a third shell.

3. The process for producing microcapsules according to claim 1, wherein the tetraalkoxysilane is added dropwise in the step during said (2) further adding, and a time of the dropwise addition of the tetraalkoxysilane is not less than 10 min and not more than 1,000 min.

4. The process for producing microcapsules according to claim 1, wherein an amount of the tetraalkoxysilane added during said (1) emulsifying is not less than 10% by mass and not more than 40% by mass on the basis of the organic compound.

5. The process for producing microcapsules according to claim 1, wherein an amount of the tetraalkoxysilane added during said (2) further adding is not less than 10% by mass and not more than 40% by mass on the basis of the organic compound.

6. The process for producing microcapsules according to claim 1, wherein the initial pH value in the sol-gel reaction of said (1) emulsifying is not less than 3.5 and not more than 4.3.

7. The process for producing microcapsules according to claim 1, wherein the initial pH value in the sol-gel reaction of said (2) further adding is not less than 2.5 and less than 3.5.

8. The process for producing microcapsules according to claim 1, wherein the organic compound present in the core is at least one material selected from the group consisting of a fragrance material, a fragrance precursor, an oil, an antioxidant and a solvent.

9. The process for producing microcapsules according to claim 2, wherein the organic polymeric compound is at least one compound selected from the group consisting of a water-soluble synthetic polymer compound and a natural polymer compound.

10. The process for producing microcapsules according to claim 1, further comprising (1-1):
    (1-1) adding a cationic polymeric compound to the water dispersion comprising the microcapsules obtained from said (1) emulsifying, wherein said (1-1) adding is carried out prior to said (2) further adding.

11. The process for producing microcapsules according to claim 1, wherein the organic compound present in the core is the fragrance precursor.

12. The process for producing microcapsules according to claim 11, wherein the fragrance precursor is a silicic acid ester comprising an alkoxy component derived from a fragrance alcohol.

13. Microcapsules each comprising a core comprising at least one organic compound, a first shell encapsulating the core, and a second shell encapsulating the first shell,
   wherein the first shell encapsulating the core comprises silica and has a thickness of not less than 5 nm and not more than 20 nm;
   wherein the second shell encapsulating the first shell comprises silica and has a thickness of not less than 10 nm and not more than 100 nm; and
   wherein the microcapsules have an average particle size of not less than 0.5 μm and not more than 50 μm.

14. The microcapsules according to claim 13, further comprising a third shell present on and in contact with the second shell, said third shell comprising an organic polymeric compound.

15. Microcapsules produced by the process according to claim 1, comprising a core comprising
   at least one organic compound,
   a first shell encapsulating the core and comprising silica, and
   a second shell encapsulating the first shell and comprising silica,
   wherein the microcapsules have an average particle size of not less than 0.5 μm and not more than 50 μm.

16. The process for producing microcapsules according to claim 1, wherein a total amount of the tetraalkoxysilane added present during the process is not less than 20% by mass and not more than 60% by mass on the basis of the organic compound.

17. The process for producing microcapsules according to claim 1, wherein the surfactant present during said (1) emulsifying is a cationic surfactant.

18. The process for producing microcapsules according to claim 10, wherein an equivalent amount of a cationic group in the cationic polymeric compound is not less than 1 meq/g and not more than 10 meq/g.

19. The process for producing microcapsules according to claim 10, wherein an amount of the cationic polymer compound added is not less than 0.05% by mass and not more than 5% by mass, based on a total amount of the organic compound in the microcapsules.

* * * * *